(12) United States Patent
Eder et al.

(10) Patent No.: US 8,735,564 B2
(45) Date of Patent: *May 27, 2014

(54) FAST RESULTS HYBRID CAPTURE ASSAY AND SYSTEM

(75) Inventors: Paul Eder, Gaithersburg, MD (US); Eric Payne, Fairfield, PA (US); Irina Nazarenko, Gaithersburg, MD (US); Suganthi Ramachandran, Fairfax, VA (US); Arvind Virmani, Germantown, MD (US); Laura Bell, Gaithersburg, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 19 days.

This patent is subject to a terminal disclaimer.

(21) Appl. No.: 13/616,899

(22) Filed: Sep. 14, 2012

(65) Prior Publication Data

US 2013/0011830 A1  Jan. 10, 2013

Related U.S. Application Data

(63) Continuation of application No. 12/605,540, filed on Oct. 26, 2009, now Pat. No. 8,288,520.

(60) Provisional application No. 61/108,687, filed on Oct. 27, 2008, provisional application No. 61/174,848, filed on May 1, 2009.

(51) Int. Cl.
*C12Q 1/68* (2006.01)
*G01N 33/53* (2006.01)
*C07K 16/00* (2006.01)
*C07H 21/04* (2006.01)
*C12N 15/11* (2006.01)

(52) U.S. Cl.
USPC .......... 536/24.3; 435/6.1; 435/7.1; 530/387.1

(58) Field of Classification Search
None
See application file for complete search history.

(56) References Cited

U.S. PATENT DOCUMENTS

| | | | |
|---|---|---|---|
| 4,486,536 A | 12/1984 | Baker et al. | |
| 4,486,539 A | 12/1984 | Ranki et al. | |
| 4,563,417 A | 1/1986 | Alabrella et al. | |
| 4,563,419 A | 1/1986 | Ranki et al. | |
| 4,689,294 A | 8/1987 | Boguslawski et al. | |
| 4,731,325 A | 3/1988 | Palva et al. | |
| 4,732,847 A | 3/1988 | Stuart et al. | |
| 4,743,535 A | 5/1988 | Carrico | |
| 4,751,177 A | 6/1988 | Stabinsky et al. | |
| 4,775,619 A | 10/1988 | Urdea | |
| 4,833,084 A | 5/1989 | Carrico | |
| 4,851,330 A | 7/1989 | Kohne et al. | |
| 4,865,980 A | 9/1989 | Stuart et al. | |
| 4,868,105 A | 9/1989 | Urdea et al. | |
| 4,889,798 A | 12/1989 | Rabbani | |
| 4,894,325 A | 1/1990 | Englehardt et al. | |
| 5,082,830 A | 1/1992 | Brakel et al. | |
| 5,106,727 A | 4/1992 | Hartley et al. | |
| 5,116,734 A | 5/1992 | Higgs et al. | |
| 5,200,313 A | 4/1993 | Carrico | |
| 5,288,611 A | 2/1994 | Kohne et al. | |
| 5,374,524 A | 12/1994 | Miller et al. | |
| 5,424,413 A | 6/1995 | Hogan et al. | |
| 5,437,977 A | 8/1995 | Segev | |
| 5,474,895 A | 12/1995 | Ishii et al. | |
| 5,484,699 A | 1/1996 | Bouma et al. | |
| 5,545,806 A | 8/1996 | Lonberg et al. | |
| 5,545,807 A | 8/1996 | Surani et al. | |
| 5,556,748 A | 9/1996 | Douglas | |
| 5,614,362 A | 3/1997 | Urdea et al. | |
| 5,623,049 A | 4/1997 | Lobberding et al. | |
| 5,627,030 A | 5/1997 | Pandian et al. | |
| 5,629,153 A | 5/1997 | Urdea | |
| 5,629,156 A | 5/1997 | Shah et al. | |
| 5,635,352 A | 6/1997 | Urdea et al. | |
| 5,641,630 A | 6/1997 | Snitman et al. | |
| 5,656,731 A | 8/1997 | Urdea | |
| 5,681,697 A | 10/1997 | Urdea et al. | |
| 5,681,897 A | 10/1997 | Silvis et al. | |
| 5,695,926 A | 12/1997 | Cros et al. | |
| 5,702,893 A | 12/1997 | Urdea et al. | |
| 5,728,531 A | 3/1998 | Yamada et al. | |
| 5,731,153 A | 3/1998 | Lucas et al. | |
| 5,736,316 A | 4/1998 | Irvine et al. | |
| 5,747,244 A | 5/1998 | Sheridan et al. | |
| 5,747,248 A | 5/1998 | Collins | |
| 5,750,338 A | 5/1998 | Collins et al. | |
| 5,759,773 A | 6/1998 | Tyagi et al. | |
| 5,786,183 A | 7/1998 | Ryder et al. | |

(Continued)

FOREIGN PATENT DOCUMENTS

AU    701781 B2    5/1997
EP    0163220    12/1985

(Continued)

OTHER PUBLICATIONS

International Preliminary Report and Written Opinion issued May 3, 2011 based on PCT/US2009/062061; 11 pp.

(Continued)

*Primary Examiner* — James Martinell
(74) *Attorney, Agent, or Firm* — Miles & Stockbridge, P.C.

(57) ABSTRACT

The present invention comprises a method that provides fast and reliable results for detecting the presence of a target nucleic acid molecule in a sample.

24 Claims, 9 Drawing Sheets

(56) References Cited

U.S. PATENT DOCUMENTS

| | | | |
|---|---|---|---|
| 5,792,606 A | 8/1998 | Deger et al. |
| 5,800,994 A | 9/1998 | Martinelli et al. |
| 5,814,492 A | 9/1998 | Carrino et al. |
| 5,821,339 A | 10/1998 | Schaffer et al. |
| 5,827,661 A | 10/1998 | Blais |
| 5,853,993 A | 12/1998 | Dellinger et al. |
| 5,888,724 A | 3/1999 | Silverstein et al. |
| 5,981,179 A | 11/1999 | Lorincz et al. |
| 5,994,079 A | 11/1999 | De La Rosa et al. |
| 6,027,897 A | 2/2000 | Lorincz et al. |
| 6,043,038 A | 3/2000 | Sivaraja et al. |
| 6,057,099 A | 5/2000 | Nathan et al. |
| 6,083,925 A | 7/2000 | Li et al. |
| 6,110,676 A | 8/2000 | Coull et al. |
| 6,110,682 A | 8/2000 | Dellinger et al. |
| 6,110,687 A | 8/2000 | Nilsen |
| 6,207,385 B1 | 3/2001 | Stanley |
| 6,221,581 B1 | 4/2001 | Engelhardt et al. |
| 6,225,053 B1 | 5/2001 | Garcia et al. |
| 6,228,578 B1 | 5/2001 | Impraim et al. |
| 6,228,580 B1 | 5/2001 | Blumenfeld et al. |
| 6,232,462 B1 | 5/2001 | Collins et al. |
| 6,268,128 B1 | 7/2001 | Collins et al. |
| 6,277,579 B1 | 8/2001 | Lazar et al. |
| 6,280,954 B1 | 8/2001 | Ulfendahl |
| 6,326,136 B1 | 12/2001 | Lazar et al. |
| 6,355,424 B1 | 3/2002 | Lorincz et al. |
| 6,436,662 B1 | 8/2002 | Mielzynska et al. |
| 6,521,190 B1 | 2/2003 | Edens et al. |
| 6,544,732 B1 | 4/2003 | Chee et al. |
| 6,583,278 B1 | 6/2003 | Carter |
| 6,686,151 B1 | 2/2004 | Lazar et al. |
| 6,828,098 B2 | 12/2004 | Langmore et al. |
| 6,890,729 B2 | 5/2005 | Mietzynska et al. |
| 6,969,585 B2 | 11/2005 | Lorincz et al. |
| 6,977,148 B2 | 12/2005 | Dean et al. |
| 7,001,776 B2 | 2/2006 | Botacini das Dores et al. |
| 7,138,505 B1 | 11/2006 | Kuo et al. |
| 7,371,518 B2 | 5/2008 | Lorincz et al. |
| 7,439,016 B1 | 10/2008 | Anthony et al. |
| 7,601,497 B2 | 10/2009 | Nazarenko et al. |
| 7,645,571 B2 | 1/2010 | Anthony et al. |
| 7,812,144 B2 | 10/2010 | Karlsen |
| 7,829,691 B2 | 11/2010 | Anthony et al. |
| 8,288,520 B2 * | 10/2012 | Eder et al. ............ 536/24.3 |
| 2001/0055766 A1 | 12/2001 | Aristarkhov et al. |
| 2002/0012936 A1 | 1/2002 | Lorincz et al. |
| 2003/0096232 A1 | 5/2003 | Kris et al. |
| 2003/0108897 A1 | 6/2003 | Drmanac |
| 2003/0175765 A1 | 9/2003 | Kessler et al. |
| 2003/0175789 A1 | 9/2003 | Weininger et al. |
| 2004/0180362 A1 | 9/2004 | Lazar et al. |
| 2004/0214302 A1 | 10/2004 | Anthony et al. |
| 2005/0032038 A1 | 2/2005 | Fisher et al. |
| 2005/0032105 A1 | 2/2005 | Bair et al. |
| 2005/0147996 A1 | 7/2005 | Sorge |
| 2006/0051809 A1 | 3/2006 | Nazarenko et al. |
| 2006/0160188 A1 | 7/2006 | Kurnit et al. |
| 2006/0240449 A1 | 10/2006 | McGlennen et al. |
| 2007/0154884 A1 | 7/2007 | Lorincz et al. |
| 2008/0200344 A1 | 8/2008 | Cheng |
| 2008/0247914 A1 | 10/2008 | Edens et al. |
| 2009/0032445 A1 | 2/2009 | Doak et al. |
| 2009/0263819 A1 | 10/2009 | Muraca |
| 2009/0286687 A1 | 11/2009 | Dressman et al. |
| 2009/0298187 A1 | 12/2009 | Nazarenko et al. |
| 2010/0036104 A1 | 2/2010 | Nazarenko et al. |
| 2010/0081124 A1 | 4/2010 | Abravaya et al. |
| 2010/0216147 A1 | 8/2010 | Upton et al. |
| 2010/0285471 A1 | 11/2010 | Croce et al. |
| 2010/0311039 A1 | 12/2010 | Lowe et al. |
| 2011/0003288 A1 | 1/2011 | Anthony et al. |
| 2011/0053143 A1 | 3/2011 | Lowe et al. |
| 2011/0059542 A1 | 3/2011 | Anthony et al. |
| 2011/0065906 A1 | 3/2011 | Liu et al. |
| 2011/0196146 A1 | 8/2011 | Khripin et al. |
| 2011/0217705 A1 | 9/2011 | O'Neill et al. |
| 2011/0294111 A1 | 12/2011 | Nazarenko |
| 2012/0004128 A1 | 1/2012 | Mallonee et al. |
| 2012/0021460 A1 | 1/2012 | Lowe et al. |
| 2012/0045756 A1 | 2/2012 | Rothmann et al. |

FOREIGN PATENT DOCUMENTS

| | | |
|---|---|---|
| EP | 0 167 366 B1 | 1/1986 |
| EP | 0 281 927 B1 | 9/1988 |
| EP | 0 288 737 A1 | 11/1988 |
| EP | 0333465 | 9/1989 |
| EP | 0 336 454 B1 | 10/1989 |
| EP | 0 144 914 A2 | 6/1995 |
| EP | 0 703 296 A1 | 3/1996 |
| EP | 89/11546 B1 | 3/1996 |
| EP | 1 806 410 A2 | 7/2007 |
| EP | 2 184 368 A1 | 5/2010 |
| JP | H07505759 A | 6/1995 |
| JP | H08505770 A | 6/1996 |
| JP | 2009106220 A | 5/2009 |
| WO | 84/02721 | 7/1984 |
| WO | 8607387 | 12/1986 |
| WO | 88/03957 | 6/1988 |
| WO | 91/08312 A1 | 6/1991 |
| WO | 93/10263 A1 | 5/1993 |
| WO | 94/16108 A1 | 7/1994 |
| WO | 95/17430 A1 | 6/1995 |
| WO | 9640992 | 12/1996 |
| WO | 9705277 | 2/1997 |
| WO | 9710364 | 3/1997 |
| WO | 97/31256 A2 | 8/1997 |
| WO | 9818488 | 5/1998 |
| WO | 9822620 | 5/1998 |
| WO | 9859044 | 12/1998 |
| WO | 99/02488 | 1/1999 |
| WO | 99/32654 A1 | 7/1999 |
| WO | 99/36571 A2 | 7/1999 |
| WO | 9949224 | 9/1999 |
| WO | 99/50459 A2 | 10/1999 |
| WO | 00/60116 A1 | 10/2000 |
| WO | 0136681 | 5/2001 |
| WO | 01/96608 A1 | 12/2001 |
| WO | 0196608 | 12/2001 |
| WO | 2004/087950 A2 | 10/2004 |
| WO | 2005080602 | 9/2005 |
| WO | 2007/056723 | 5/2007 |
| WO | 2007/130519 A2 | 11/2007 |
| WO | 2008/036061 A2 | 3/2008 |
| WO | 2008/139938 A1 | 11/2008 |
| WO | 2009/057993 A1 | 5/2009 |
| WO | 2009/123996 A2 | 10/2009 |
| WO | 2010/004251 A1 | 1/2010 |
| WO | 2010/028382 A2 | 3/2010 |
| WO | 2010/127228 A1 | 11/2010 |

OTHER PUBLICATIONS

International Search Report mailed Apr. 13, 2010 based on PCT/US2009/062061; 7 pp.

International Preliminary Report on Patentability and Written Opinion issued May 3, 2011 based on PCT/US2009/062041; 8 pp.

International Preliminary Report on Patentability and Written Opinion issued Nov. 1, 2011 based on PCT/US2010/033145; 7 pp.

International Search Report and Written Opinion mailed Aug. 5, 2010 based on PCT/US1O/33145; 8 pp.

Invitrogen: "Anti-V5 Antibody, Anti-V5-HRP Antibody" Jan. 1, 2001; pp. 1-13.

International Preliminary Report on Patentability and Written Opinion based on PCT/US2010/047769 mailed Mar. 6, 2012.

International Preliminary Report on Patentability and Written Opinion based on Application No. PCT/US2010/048714 dated Mar. 20, 2012 (8 pages).

International Search Report and Written Opinion based on application No. PCT/US2011/037012 dated Apr. 17, 2012 (20 pages).

Belousov et al.; "Single Nucleotide Polymorphism Genotyping by Two Colour Melting Curve Analsis Using the MGB Eclipse Probe

(56) References Cited

OTHER PUBLICATIONS

System in Challenging Sequence Environment"; Human Genomics; Mar. 2004; vol. 1; No. 3; pp. 209-217.
U.S. Appl. No. 12/605,605; Office Action mailed Dec. 7, 2011 (19 pages).
U.S. Appl. No. 12/605,605; Office Action mailed May 8, 2012 (22 pages).
International Search Report and Written Opinion of PCT/US2011/22887, dated Jun. 1, 2011.
International Preliminary Report on Patentability and Written Opinion of PCT/US2009/062061, dated May 12, 2011.
International Preliminary Report on Patentability and Written Opinion of PCT/US2009/062041, dated May 12, 2011.
GenBank Submission FJ429103. 2009 [Retrieved from the Internet May 20, 2011: <URL:http://www.ncbl.nlm.nih.gov/nuccore/FJ429103.1>]; in entirety.
Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.
Partial European Search Report of EP10185824: mailed Feb. 16, 2011 (8 pages).
Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.
Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.
International Search Report and Written Opinion of PCT/US2010/048714, dated Dec. 10, 2010 (14 pages).
International Preliminary Report on Patentability and Written Opinion of PCT/US2009/041033, dated Oct. 19, 2010 (6 pages).
International Search Report and Written Opinion of PCT/US2010/047769, dated Nov. 9, 2010 (11 pages).
Pachowics, et al., "Sequence specific large volume sample prep solution utilizing Hybrid Capture technology," 41st Annual Oak Ridge Conference; Baltimore, MD; Apr. 16, 2009; retrieved from the Internet: http://www.aacc.org/events/meeting_proceeding/2009/Documents/OakRidge09AllPosters.pdf.
Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott -Raven Publishers, XP008011933.
Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.
Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.
Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.
Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6. (Note that the page number of this literature listed on the ISR is incorrect).
Vernick et al., "The HPV DNA virus hybrid capture assay: What is it- and where do we go from here?" MLO Med. Lab. Obs., (Mar. 2003), pp. 8-10, 13, vol. 35, No. 3.
Supplementary European Search Report of PCT/US2006/060603, dated Jul. 7, 2010 (8 pages).
International Search Report and Written Opinion of PCT/US2010/022264 dated Jun. 7, 2010 (19 pages).
Cohenford et al., "C-195. Rapid Detection of *Chlamydia trachomatis* from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "Chlamydia DNA Test Kit," (Jun. 6, 2008), XP002578832, Retrieved from the Internet: URL: http://www.gentechin.com/chlamydiatestkit.htm.
Taha et al., "Universal Collection Medium (UCM) is as suitable as the Standard Transport Medium (STM) for Hybrid Capture II(HC-2) assay," Journal of Clincal Virology, (May 1, 2006), pp. 32-35, vol. 36, No. 1, XP005367693.
Darwin et al., "Comparison of Digene Hybrid Capture 2 and Conventional Culture for Detection of *Chlamydia trachomatis* and *Neisseria gonorrhoeae* in Cervical Specimens," Journal of Clinical Microbiology, (Feb. 2002), pp. 641-644, vol. 40, No. 2, XP002578833.
Nazarenko et al., "A novel method of HPV genotyping using Hybrid Capture sample preparation method combined with GP5+/6+PCR and multiplex detection on Luminex XMAP," Journal of Clinical Virology, (Dec. 1, 2008), pp. 76-81, vol. 154, No. 1-2, XP025680302.
International Search Report for PCT/US2009/062041, Patent Cooperation Treaty, Mar. 31, 2010 (17 pages).
Mittendorf T, et al., "HPV-DNA-Diagnostik zur Zervixkarzinofrüherkennung;Deutsche Agentur für HTA des Deutschen Instituts für Medizinische Dokumentation und Information," 1. Auflage 2007, pages 2, 5, and 6 only.
Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.
Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.
Malloy C, et al., "HPV DNA Testing: Technical and Programmatic Issues or Cevical Cancer Prevention in Low-Resouce Settings," Path, Dec. 2000.
Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031. Nov. 1995.
Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).
Bohm S, et al., "The Predominant mRNA Class in HPV16-Infected Genital Neoplasias does not Encode the E6 or the E7 Protein," Int. J. Cancer: 55, 791-798 (1993).
Middleton, K, et al., "Organization of Human Papillomavirus Productive Cycle during Neoplastic Progression Provides a Basis for Selection of Diagnostic markers," Journal of Virology, Oct. 2003, pp. 10186-10201.

(56) References Cited

OTHER PUBLICATIONS

Letter dated Jan. 6, 2010 to EPO re EP 1 038 022 (46 pages).
Letter to EPO dated Mar. 2, 2009 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Partial International Search Report for PCT/US2009/062061, mail date Jan. 5, 2010.
Partial International Search Report for PCT/US2009/062041, mail date Jan. 5, 2010.
Bhan P, et al., "2', 5'-linked oligo-3'-deoxyribonucleoside phosphorothioate chimeras: thermal stability and antisense inhibition of gene expression," Nucleic Acids Research Aug. 15, 1997, vol. 25, No. 16, pp. 3310-3317, XP002560367, ISSN: 0305-1048, p. 3313.
Genetech Diagnostics Pvt. Ltd., "Digene HBV Test Hybrid Capture II," Jun. 6, 2008, XP-00256068, retrieved from internet: URL:http://www.gentechin.com/hbvdnatestkit.htm>, the whole document.
Hantz S, et al., "[Evalutation of accuracy of three assays for human papillomavirus detection and typing: Hybrid Capture 2, HPV Consensus kit and Amplicor HPB.]," Pathologie-Biologie, Feb. 2008, vol. 56, No. 1, Feb. 2008, pp. 29-35, XP 002560369, ISSN: 0369-8114, the whole document, Abstract Only.
Sandri et al., "Comparison of the Digene HC2 Assay and the Roche Amplicor Human Papillomavirus (HPV) Test for Detection of High-Risk HPV Genotypes in Cervical Samples," Journal of Clinical Microbiology, Jun. 2006, vol. 44, No. 6, pp. 2141-2146, XP002560370, ISSN: 0095-1137, the whole document.
Boston Bioproducts Inc., "Protein Extraction buffers," Sep. 2, 2007, XP002560371, Retrieved from the Internet: URL: http://www.bostonbioproducts.com/product_disply1.php?page=20&limit=10&id=4>, the whole document.
Bart "General Principles of Immunoprecipitation," Jul. 31, 2008, XP002560372, URL:http://pingu.salk.edu/{sefton/Hyper_protocols/immunoprecip.html>, the whole document. Li.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) and Poly(I) Poly(dC) as Immunogens for the Induction of Antibodies to RNA-DNA Hybrids," Molecular Immunology, vol. 19, No. 3, pp. 413-420, 1982.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.
Jakobovits et al., "Germ-line transmission and expression of a human-derived yeast artificial chromosome," pp. 255-258, Nature, vol. 362, Mar. 18, 1993.
U.S. Appl. No. 12/588,304, titled "Automated Assay and System," filed Oct. 9, 2009 (not yet published).
U.S. Appl. No. 12/588,306, titled "Open Platform Automated Sample Processing System," filed Oct. 9, 2009 (not yet published).
U.S. Appl. No. 12/622,131, titled "Multiple-Input Analytical System," filed Nov. 19, 2009 (not yet published).
U.S. Appl. No. 12/605,540, titled "Fast Results Hybrid Capture Assay and System," filed Oct. 26, 2009 (not yet published).
U.S. Appl. No. 12/605,605, titled "Fast Results Hybrid Capture Assay on an Automated Platform," filed Oct. 26, 2009 (not yet published).
International Search Report for PCT/US2009/041033, dated Deember 22, 2009.
Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1), pp. 17-27—see table 3.
GenBank Accession No. K02718, "Human papillomavirus type 16 (HPV16), complete genome.", Mar. 18, 1994. See http://www.ncbi.nlm.nihgov/nuccore/333031.
GenBank Accession No. X74479, "human papillomavirus type 45 genomic DNA.", Apr. 18, 2005. See http://www.ncbi.nlm.nih.gov/nuccore/397022.
GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002. See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi.nlm.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.
GenBank Accession No. X77858, "Human papillomavirus type 59, complete viral genome.", Apr. 18, 2005. See http://www.ncbi.nlm.nih.gov/nuccore/557236.
GenBank Accession No. U31794, "Human papillomavirus type 66, complete genome.", Oct. 18, 1995. See http://www.ncbi.nlm.nih.gov/nuccore/1020290.
GenBank Accession No. X67161, "Human papillomavirus type L1 gene for major capsid protein.", Apr. 18, 2005. See http://www.ncbi.nlh.nih.gov/nuccore/1197494.
GenBank Accession No. AB027021, "Human papillomavirus type 82 DNA, complete genome.", Jun. 22, 2000. See http://www.ncbi.nlm.nih.gov/nuccore/6970427.
Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517, see the whole document.
Lowe, et al., "A computer program for select of oligonucleotide polymerase chain reactions", Nucleic Acid Res., vol. 18, No. 7, pp. 1757-1761 (1990).
Broker et al., "A Molecular Portrait of Human Papillomavirus Carcinogenesis", Cancer Cells, vol. 7, pp. 197-208, 1989 (Roche EU Opposition).
Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).

(56) References Cited

OTHER PUBLICATIONS

Karlsen et al., "Use of Multiple PCR Primer Sets for Optimal Detection of Human Papillomavirus", Journal of Clinical Microbiology, pp. 2095-2100. Sep. 1996 (Roche EU Opposition).
Park et al., "Physial Staus and Expession of HPV Genes in Cevical Cancers"Gyneclogic Oncology, vol. 65, pp. 121-129, 1997 (Roche EU Opposition).
Stoler et al., "Human Papillomavirus Type 16 and 18 Gene Expression in Cervical Neoplasias", Human Pathology, vol. 23, No. 2, pp. 117-128, Feb. 1992 (Roche EU Opposition).
De Villiers et al., "Classification of Papillomaviruses", Virology, vol. 324, pp. 17-27, 2004.
Howley et al., "A Rapid Method for Detecting and Mapping Heterologous DNAs", Journal of Biological Chemisny, vol. 254, No. 11, pp. 4879-4883, Jun. 10, 1979.
Law et al., "Conserved Polynucleotide Sequences Among the Genomics of Papillomaviruses", Journal of Virology, vol. 32, No. 1, pp. 199-207, Oct. 1979.
Heilman et al., "Cloning of Human Papilloma Virus Genomic DNAs and Analysis of Homologous Polynucleotide Sequences", Journal of Virology, vol. 36, No. 2, pp. 395-407. Nov. 1980.
Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.
Lorincz, A.T., "Molecular Methods for the Detection of Human Papillomavirus Infection", Obstetrics and Gynecology Clinics of North America, vol. 23, No. 3, pp. 707-730. Sep. 1996.
Blair et al. "Herpes Simplex Virus Viron Stimulatory Protein mRNA Leader Contains Sequence Elements Which Increase Both Virus-Induced Transcription and tnRNA Stability," Journal of Virology, vol. 61, No. 8, pp. 2499-2508, Aug. 1987.
Chandler et al., 'Detection of Dengue-2 Viral RNA by Reversible Target Capture Flybridization., J. Clin. Micobiol., vol. 31 (10), pp. 2641-2647, 1993.
Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Microbiol., vol. 37, No. 4, pp. 958-963, 1999.
Murakami et al., Fluorescent-Labeled Oligonucleotide Probes: Detection of Hybrid Formaton in Solution by Fluorscence Polarization Spectroscopy, Nucleic Acids Res., vol. 19 (15), pp. 4097-4102, 1991.
Dunn and Hassell: "A Novel Method to Map Transcripts: Evidence for Homology between an Adenovirus niRNA and Discrete Multiple Regions of the Viral Genome" Cell, 12:23-36, Sep. 1977.
Coutlee et al., "Nonisotopic Detection of RNA in an Enzyme Imunoassay using a Monoclonal Antibody Against DNA-RNA Hybrids" Analytical Biochemistry 181:153-162, 1989.
Chen et al., "DNA Optical Sensor: A Rapid Method for the Detection of DNA of Hybridization" Biosensors & Bioelectronics 13:451-458, 1998.
Chevrier et al., "Isolation of a Specific DNA fragment and Development of a PCR Based Method for the Detection of Mycobacterium genavense" FEMS Immunology and Medical Microbiology 23:243-452, 1999.
Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 26:5581-5588, 1998.
Gelmetti et al., "Detection of Rabbit Haemorrhagic Disease Virus (RHVD) by in Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detection of Salmonella by Using the Colorimetric DNA/rRNA Sandwich Hybridization in Microtiter Wells" J. Vet. Med. Sci. 62:615-619, 2000.

Lazar et al., 1999 "Hybrid Capture®: a Sensitive Signal Amplification-based Chemiluminescent Test for the Detection and Quantitation of Human Viral and Bacterial Pathogens".1. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture"MoL Cell Probes 3:375-382.
Lamoureux et al., 1997 "Detection of Campylobacter jejuni in Food and Poultry Viscera Using Immunomagnetic Separation and Microtitre Hybridization" J. Appl. Microbiol. 83:641-651.
Coutlee et al., 1990 "Quantitative Detection of Messenger RNA by Solution Hybridization and Enzyme Immunoassay'" Biol. Chem. 265:11601-11604.
Stollar, B.D. and A. Rashtchian, 1987 "Immunochemical Approaches to Gene Probe Assays" Anal. Biochem. 161:387-394.
Blais B.W., 1994 "Transriptional Enhancement of the Listeria Monocytogenes PCR and Simple Immunoenzymatic Assay of the Product Using Anti-RNA:DNA Antibodies" AppL Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbiol. 27:120-125.
Boguslawski et al., 1986 "Characterization of Monoclonal Antibody to DNA:RNA and Its Application to Immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids". Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Colorimetric Fluoescent and Enzymatc Amplification Substrate Systems in an Enzyme Immunoassay for Detection of DNA-RNA Hybrids" J. Clin. Microbiol. 27:1002-1007.
Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.
McLauchlan et al., DNA sequence homology between two co-linear loci on the HSV genome which have different transforming abilities, The EMBO Journal, 1983, vol. 2, No. 11, pp. 1953-1961.
Goldsborough et al., Nucleotide Sequence of Human Papillomavirus Type 31: A Cervical Neoplasia Associated Virus, Virology, 1989, vol. 171, pp. 306-311.
McGeoch et al., "DNA Sequence and Genetic Content of the Hindlll 1 Region in the Short Unique Component of the Herpes Simplex Virus Type 2 Genome; Identification of the Gene Encoding Glycoprotein G, and Evolutionary Comparisons," J. Gen. Virol., 1987, vol. 68, pp. 19-38.
McGeoch et al., The Complete DNA Sequence of the Long Unique Region in the Genome of Hepes Simplex Virus Type I, 1 Gen Virol., 1988, vol. 69, pp. 1531-1574.
Yamada et al., Human Papillomavirus Type 16 Variant Lineages in United States Populations Characterized by Nucleotide Sequence Analysis of the E6, L2, and L1 Coding Segments, J. Virol., Dec. 1995, vol. 69, No. 12, pp. 7743-7753.
Swain et al., Nucleotide Sequence of the Herpes Simplex Virus Type 2 Thymidine Kinase Gene,' Virol., Jun. 1983, vol. 46, No. 3, pp. 1045-1050.
Delius et al., Primer-Directed Sequencing of Human Papillomavirus Types, Current Topics in Microbiology and Immunology, 1994, vol. 185, pp. 13-31.
Larder et al., Related functional domains in virus DNA polymerases, The EMBO J., 1987, vol. 6, No. 1, pp. 169-175.
McGeoch et al., Structures of Herpes Simplex Virus Type 1 Genes Required for Replica on of Virus DNA, J. Virol., vol. 62, No. 2, pp. 444-453.

(56) References Cited

OTHER PUBLICATIONS

Zientara et al., 1998 "Use of reverse transciptase-polymerase chain reaction (RT-PCR )and dot-blot hybridization for the dectection and identification of African horse sickness virus nucleic acids" Arch Virol 14:317-327.

Mansy et al., 1999 "A PCR Based DNA Hybridisation Capture System for the Detection of Human Cytomegalovirus. A Comparative Study with Other Identification Methods" Journal of Virological Methods 80:113-122.

Poulsen et al., 1999 "Detection of Clinical Vancomycin-Resisant *Enterococci* in Denmark by Multiplex PCR and Sandwich Hybridization" APMIS 107:404-12.

Sjoroos et al., 1998 "Time-Resolved Fluorometry Based Sandwich Hybrdisation Assay for HLA-DQA1 Typing" Disease Markers 14:9-19.

Edman et al., 2000 "Pathogen Analysis and Genetic Predisposition Testing Using Microelectronic Arrays and Isothermal Amplification" Journal of Investigative Medicine, 48:93-101.

Monteiro et al.,1997 Evaluation of Performances of Three DNA Enzyme Immunoassays for Detection of Helicobacter pylori PCR Products from Biopsy Specimens Journal of Clinical Microbiology, 35:2931-2936.

Chiu et al., 1998 "Sandwich-type Deoxyribonucleic Acid Hybridization Assays Based on Enzyme Amplified Time-Resolved Fluorometry" Analyst , 123:1315-1319.

White et al., 1999 "Signal Amplification System for DNA Hybridization Assays Based on in vitro Expression of a DNA Label Encoding Apoaequorin" Nucleic Acids Research 27:i-viii.

Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.

Zammatteo et al., 1997 "Comparison between Microwell and Bead Supports for the Detection of Human Cytomegalovirus Amplicons by Sandwich Hybridization" Analytical Biochemistry 253:180-189.

Fisher et al., 1997 "A System for the Quantitation of DNA Using a Microtiter Plate-Based Hybridization and Enzyme Amplification Technology" Analytical Biochemistry 251:280-287.

Wicks et al., 1998 "A Sandwich Hybridization Assay Employing Enzyme Amplification for Determination of Specific Ribosomal RNA from Unpurified Cell Lysates" Analytical Biochemistry 259:258-264.

Bruckner-Lea et al., 2000 "Rotating Rod Renewable Microcolumns for Automated, Solid-Phase DNA Hybridization Studies" Anal. Chem. 72:4135-4141.

Allen et al., 1998 "High Resolution Genetic Typing of the Class II HLA-DRB 1 Locus Using Group-Specific Amplification and SSO-Hybridisation in Microplates" Hereditas 129:161-167.

Chomvarin et al., 2000 "Development of EIA for Detection of *Chlamydia trachomatis* in Genital Specimens"The Southeast Asian Journal of Tropical Medicine and Public Health, 31:96-103.

Alexandre et al., 1998 "Quantitative Determination of CMV DNA Using a Combination of Competitive PCR Amplification and Sandwich Hybridization" BioTechniques, 25: 676-683.

Casademont et al., 2000 "Rapid Detection of Campylobacter fetus by Polymerase Chain Reaction Combined With Non-Radioactive Hybridization Using an Oligonucleotide Covalently Bound to Microwells" Molecular and Cellular Probes 14:233-240.

Hara et al., "Small Sample Whole-Genome Amplification," Optics East 2005, UCRL-PROC-216415, Lawrence Livermore National Laboratory, Oct. 21, 2005.

Brigotti, et al., Nucleic Acids Res., vol. 26, No. 18, pp. 4306-4307, 1998.

International Search Report Based on Application No. PCT/US2012/020684 Mailed Oct. 25, 2012.

Clad et al.; "Performance of the Aptima High-Risk Human Papillomavirus MRNA Assay in a Referral Population in Comparison With Hybrid Capture 2 and Cytology"; Journal of Clinical Microbiology; Mar. 2011; LNKD-PUBMED:21191046; vol. 49; No. 3; Dec. 29, 2010; pp. 1071-1076; Abstract.

Li et al; Detection of Human Papillomavirus Genotypes With Liquid Bead Microarray in Cervical Lesions of Northern Chinese Patients; Cancer Genetics and Cytogenetics, Elsevier Science Publishing, NewYork, NY, US; vol. 182; No. 1; Mar. 6, 2008; pp. 12-17; Abstract.

Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.

Han et al.; "Simultaneous Amplification and Identification of 25 Human Papillomavirus Types With Templex Technology"; Journal of Clinical Microbiology 200611 US LNKD-DOI:10.1128/JCM.01762-06; vol. 44; No. 11; Nov. 2006; p. 4157-4162; Abstract.

Database EMBL [Online]; Jul. 19, 2007; "Sequence 25 From Patent EP1806410"; XP002675256; Retrieved From EBI Accession No. EMBL:CS642417; Database Accession No. CS642417; The Whole Document.

Database EMBL [Online]; Dec. 14, 2010; "Sequence 26 From Patent US 7812144"; XP00267527; Retrieved From EBI Accession No. EMBL:GX640151; Database Accession No. GX640151; The Whole Document.

Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.

Database Geneseq [Online]; January 22, 2009; "HPV-16 E7/E6 Gene Target Sequence, Bases 698-720"; XP002675259 Retrieved From EBI Accession No. GSN:ATS82290; Database Accession No. ATS82290; The Whole Document.

Database Geneseq [Online]; Apr. 1, 2010; "HPV16 E7 Gene Forward RT-PCR Primer SEQ ID 49"; XP002675260; Retrieved From EBI Accession No. GSN:AXU96631; Database Accession No. AXU96631; The Whole Document.

Database Geneseq [Online]; Apr. 21, 2005; "E7 Coding Region (1-87) Amplifying Sense PCR Primer, SEQ ID No: 37"; XP002675261; Retrieved From EBI Accession No. GSN:ADX15568; Database Accession No. ADX15568; Sequence.

Lowe et al; "A Hybrid-Capture Assay to Detect HPV MRNA Ratios in Cervical Specimens"; Journal of Virological Methods; vol. 179; No. 1; Jan. 2012; pp. 142-147.

International Search Report Based on Application No. PCT/US2012/026380 Mailed Oct. 15, 2012.

Chinese Office Action (Second) issued in Application No. 200980143682.9, dated Aug. 5, 2013, and English translation thereof.

Instructions RIPA Buffer (No. 89900 89901) [online] Thermo Scientific, 2006, [<Retrieved from the Internet: http://www.piercenet.com/instructions/2161782.pdf>].

Japanese Notice of Reasons for Rejection dated Nov. 27, 2013, issued in Application No. 2011-533405 and English translation thereof.

\* cited by examiner

FAST RESULTS HYBRID CAPTURE ASSAY AND SYSTEM

This application is a Continuation application of U.S. application Ser. No. 12/605,540, filed Oct. 26, 2009, which claims priority to both U.S. Provisional Patent Application No. 61/108,687, filed Oct. 27, 2008 and U.S. Provisional Application No. 61/174,848, filed May 1, 2009. The contents of all applications are hereby incorporated by reference in their entireties.

FIELD

The present invention relates to methods, reagents, systems, and kits for determining the presence of a nucleic acid in a sample.

BACKGROUND

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations.

For example, the RNA or DNA for many microorganisms and viruses have been isolated and sequenced. Nucleic acid probes have been examined for a large number of infections. Detectable nucleic acid sequences that hybridize to complementary RNA or DNA sequences in a test sample have been previously utilized. Detection of the probe indicates the presence of a particular nucleic acid sequence in the test sample for which the probe is specific. In addition to aiding scientific research, DNA or RNA probes can be used to detect the presence of viruses and microorganisms such as bacteria, yeast and protozoa as well as genetic mutations linked to specific disorders in patient samples.

Nucleic acid hybridization probes have the advantages of high sensitivity and specificity over other detection methods and do not require a viable organism. Hybridization probes can be labeled, for example with a radioactive substance that can be easily detected, or with biochemical markers such as, for example, biotin, that allows for their capture and detection. Nucleic acid molecules may also by captured by a first antibody that is specific to DNA hybrids, wherein the hybrids may comprise DNA-RNA hybrids, DNA-DNA hybrids or RNA-RNA hybrids. The hybrids may subsequently be detected by a second, labeled, antibody that may be, for example, labeled with a biochemical marker such as alkaline phosphatase or any other marker capable of detection.

As nucleic acid sequence data for genes from humans and pathogenic organisms accumulates, the demand for fast, cost-effective, and easy-to-use tests increases. There is a need to provide novel and effective methods, compositions, and kits for determining target nucleic acids in a rapid, cost-effective, and reliable manner in geographical areas where access to medical care is not readily available. There is also a need to provide these assays in a rapid-screen format that can be used in developing countries. The methods and assays of the present invention meet these needs and may be used in manual, partially automated, automated, and non-automated systems.

Clinical analysis in developing countries and geographical areas where access to medical care is not readily available presents unique challenges. The invention described herein achieves an acceptable resolution that balances the importance of these challenges in such countries and areas. For instance, speed in obtaining results is particularly important in locations where women travel great distances to provide specimens for analysis. In such locations, it is advantageous that results are obtained within several hours or the same day while the patient is still present to avoid loss to follow-up associated with traveling from home to the test site.

Other factors facing developing countries are the cost of running the assay and the instrumentation needed to run the assay. Repeat pipettors and single pipettes are just two types of devices that are routinely used in developed countries but are potentially cost prohibitive in developing countries. Accordingly, there is a need for medical devices and products which employ cheaper and more readily accessible alternatives in developing countries.

SUMMARY

One aspect relates to a method for determining the presence of a target nucleic acid molecule in a sample containing biological material. The biological material can include a cervical epithelial cell or nucleic acid from a cervical cell. Using the disclosed methods, the determination of whether a target nucleic acid molecule is present in a sample can be obtained relatively rapidly, for example within a period of less than about two or three hours.

In an aspect, a method for determining the presence of a target nucleic acid molecule in a sample comprises:
 a) suspending the sample in a collection medium;
 b) releasing target nucleic acid molecules from the sample into the collection medium;
 c) converting double-stranded target nucleic acid molecules to single-stranded target nucleic acid molecules;
 d) contacting one or more probes with the single-stranded target nucleic acid molecules under conditions that allow the probes and target single-stranded target nucleic acid molecules to hybridize forming double-stranded nucleic acid hybrids;
 e) capturing the double-stranded nucleic acid hybrids;
 f) separating the double-stranded nucleic acid hybrids from un-bound single-stranded target nucleic acid molecules; and
 g) detecting the double-stranded nucleic acid hybrids, thereby indicating the presence of the target nucleic acid.

In one aspect, the method may be predominantly manual, requiring human input. Another aspect relates to the rapid detection of target nucleic acid molecules in a sample. The detection method may be automated, either fully automated, or partially automated—in other words requiring some human input.

Another aspect relates to the detection of target nucleic acid molecules in multiple samples at the same time or within a very short period of time, for example in a machine or a series of machines.

Yet another aspect relates to an instrument for running a method for the detection of a target nucleic acid molecule in a simple footprint. The instrument combines many, or all, of other individual instruments that perform the steps of the method.

Another aspect relates to a portable system for evaluating the detection of a target nucleic acid molecule in a sample.

Another aspect relates to a kit for the detection of a target nucleic acid molecule in a sample.

A further aspect relates to reagents within a collection medium into which a sample containing a target nucleic acid molecule are collected. The target nucleic acid molecule can be kept in the collection medium with minimal degradation of the target nucleic acid molecule over a time period of weeks or months. In an aspect, DNA-based target sample material can be kept in the collection medium with minimal degradation of the target nucleic acid molecule over a time period of weeks or months. In an aspect the detergent-based collection medium allows for the rapid analysis and processing of a sample.

DETAILED DESCRIPTION

Figure 1:
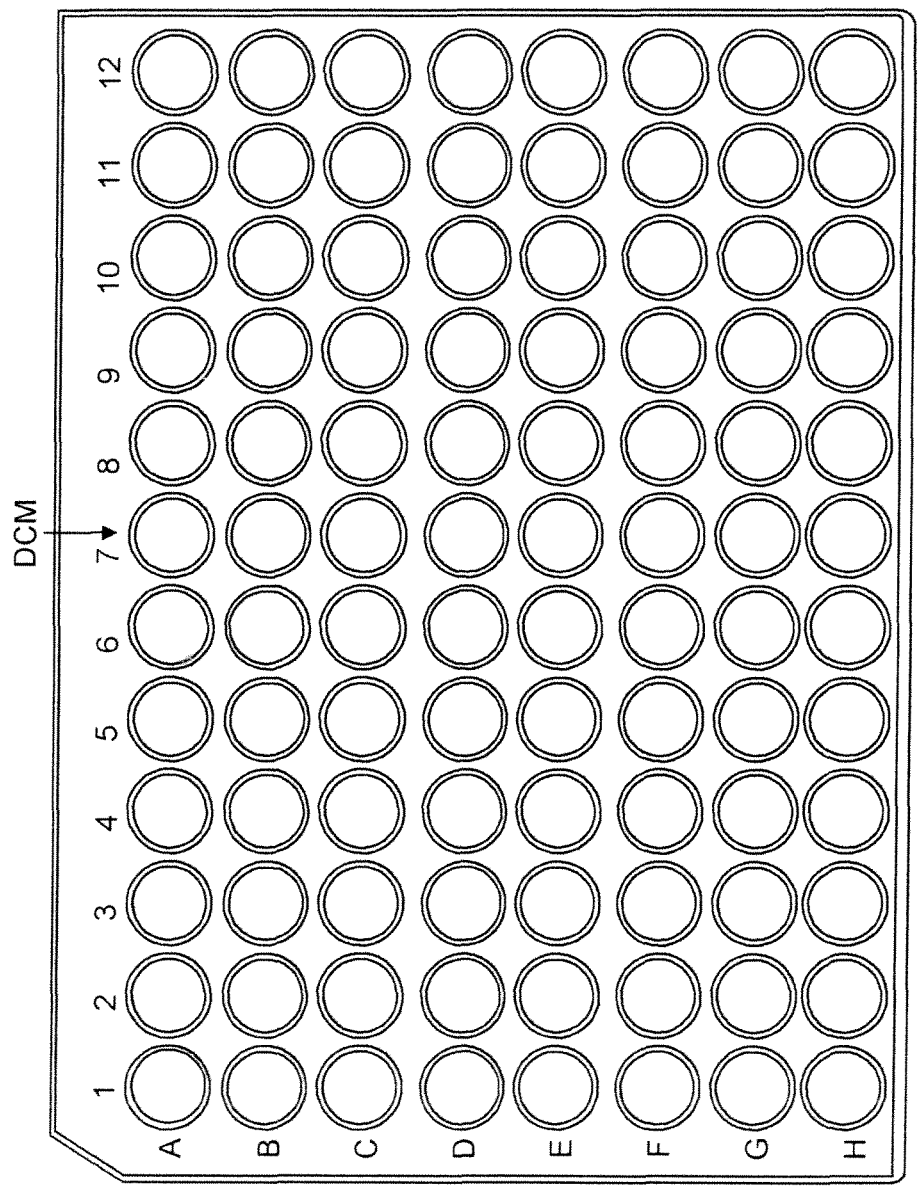
FIG. 1 shows that the detergent-based collection medium holds magnetic beads in microtiter plate wells better than known collection or sample transport medium (STM) (non-detergent based medium).

The present disclosure covers methods, compositions, reagents, systems, and kits for rapidly determining the presence of a nucleic acid molecule in a sample. The methods, compositions, reagents, systems, and kits may be used for clinical diagnostic purposes, including but not limited to the detection and identification of pathogenic organisms and the detection of a genetic predisposition to a particular disease.

In one aspect, the present disclosure provides a method for determining the presence of a target nucleic acid molecule in a sample. The method comprises:
 a) suspending the sample in a collection medium comprising a detergent;
 b) denaturing the target nucleic acid molecule;
 c) contacting one or more polynucleotide probes with the target nucleic acid molecule under conditions that allow the probes and the target nucleic acid molecule to hybridize, thereby forming a double-stranded nucleic acid hybrid;
 d) capturing the double-stranded nucleic acid hybrid on a solid support coated with a first antibody specific for the double-stranded hybrid nucleic acid hybrid, thereby forming a double-stranded nucleic acid hybrid/solid support complex;
 e) separating the double-stranded nucleic acid hybrid/solid support complex from unbound nucleic acid;
 f) conjugating the complex with a second antibody that is specific for either the double-stranded nucleic acid hybrid or specific for the first antibody to form a double-stranded nucleic acid hybrid/solid support antibody complex; wherein the second antibody is labeled with a detectable marker;
 g) washing the double-stranded nucleic acid hybrid/solid support antibody complex with a wash buffer comprising a detergent; and
 h) detecting the label on the second antibody wherein the detecting indicates the presence of the target nucleic acid molecule.

In another aspect, the present disclosure provides a method for determining the presence of a target nucleic acid molecule in a sample including suspending a sample in a collection medium including a detergent; denaturing a target nucleic acid molecule; contacting one or more polynucleotide probes with the target nucleic acid molecule under conditions that allow the probes and the target nucleic acid molecule to hybridize or bind, and capturing the double-stranded nucleic acid hybrid on a solid support coated with a first antibody specific for the double-stranded hybrid nucleic acid hybrid.

In an aspect, the present disclosure provides a method for determining the presence of a target nucleic acid molecule in a sample including suspending a sample in a collection medium including a detergent; denaturing a target nucleic acid molecule; contacting one or more polynucleotide probes with the target nucleic acid molecule under conditions that allow the probes and the target nucleic acid molecule to hybridize or bind, capturing the double-stranded nucleic acid hybrid on a solid support coated with a first antibody specific for the double-stranded hybrid nucleic acid hybrid and separating the double-stranded nucleic acid hybrid/solid support complex from unbound nucleic acid.

In an aspect, the present disclosure provides a method for determining the presence of a target nucleic acid molecule in a sample including suspending a sample in a collection medium including a detergent; denaturing a target nucleic acid molecule; contacting one or more polynucleotide probes with the target nucleic acid molecule under conditions that allow the probes and the target nucleic acid molecule to hybridize or bind, capturing the double-stranded nucleic acid hybrid on a solid support coated with a first antibody specific for the double-stranded hybrid nucleic acid hybrid, thereby forming a double-stranded nucleic acid hybrid/solid support complex; separating the double-stranded nucleic acid hybrid/solid support complex from unbound nucleic acid; and conjugating the complex with a second antibody that is specific for either the double-stranded nucleic acid hybrid or specific for the first antibody to form a double-stranded nucleic acid hybrid/solid support antibody complex.

In another aspect, the present disclosure provides a method for determining the presence of a target nucleic acid molecule in a sample including suspending a sample in a collection medium including a detergent; denaturing a target nucleic acid molecule; contacting one or more polynucleotide probes with the target nucleic acid molecule under conditions that allow the probes and the target nucleic acid molecule to hybridize or bind, capturing the double-stranded nucleic acid hybrid on a solid support coated with a first antibody specific for the double-stranded hybrid nucleic acid hybrid, thereby forming a double-stranded nucleic acid hybrid/solid support complex; and separating the double-stranded nucleic acid hybrid/solid support complex from unbound nucleic acid; conjugating the complex with a second antibody that is specific for either the double-stranded nucleic acid hybrid or specific for the first antibody to form a double-stranded nucleic acid hybrid/solid support antibody complex; wherein the second antibody is labeled with a detectable marker; and washing the double-stranded nucleic acid hybrid/solid support antibody complex with a wash buffer comprising a detergent.

In another aspect, the present disclosure provides a method for determining the presence of a target nucleic acid molecule in a sample, the method comprising:
a) suspending the sample in a collection medium comprising a detergent;
b) denaturing the target nucleic acid molecule in the sample;
c) forming a double-stranded nucleic acid hybrid by contacting at least one polynucleotide probe with the target nucleic acid molecule;
d) forming a double-stranded nucleic acid hybrid-support complex by capturing the double-stranded nucleic acid hybrid on a support, wherein the support comprises a first antibody;
e) forming a double-stranded nucleic acid hybrid-support-second antibody complex by contacting the double-stranded nucleic acid hybrid-support complex with a second antibody, wherein the second antibody is labeled with a detectable marker;
f) washing the double-stranded nucleic acid hybrid-support-second antibody complex with a wash buffer; and
g) detecting the marker on the second antibody wherein the detecting indicates the presence of the target nucleic acid molecule.

In one aspect, the solid support comprises a modified paramagnetic bead that is coated or has attached thereto a first antibody immunospecific for double-stranded hybrid nucleic acids. A magnetic field is used to separate the double-stranded nucleic acid-magnetic bead-antibody complex from non-bound nucleic acid.

In an aspect, the method does not include a sample pre-treatment step. For example, the detergent-based collection medium allows for reduced sample preparation time which, in turn, can lead to accelerated detection of target nucleic acid molecules. The sample can be analyzed by methods, assays, or the apparatus of the disclosure in a direct-to-assay manner. In an example, purification steps are not performed on the sample prior to evaluation using assays of the disclosure. In an aspect, crude lysate is directly analyzed by the methods, assays, or the apparatus of the disclosure. In another aspect, the sample does not undergo a target amplification step.

One aspect relates to a method of diagnosing cancer by utilizing methods, kits, assays, and the apparatus provided herein. In one aspect, cervical cancer is detected by identifying nucleic acid molecules associated with HPV and HPV variants. In another aspect, cervical intraepithelial neoplasia (CIN) can be screened for using methods, kits, assays, and the apparatus provided herein. The detected cancer can be subsequently treated after being diagnosis by the methods, kits, assays, and the apparatus provided herein. In an aspect, the diagnosed cancer is cervical cancer and variants thereof.

In one aspect, the disclosure provides a composition comprising a biological sample suspended in a collection medium comprising about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide.

In an aspect, the disclosure provides for a composition comprising
(a) a biological sample suspended in about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide; and
(b) at least one or more polynucleotide probes.

In an aspect, the disclosure provides for a composition comprising
(a) a biological sample suspended in a collection medium comprising about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide;
(b) at least one or more polynucleotide probes; and
(c) a first antibody.

In an aspect, the disclosure provides for a composition comprising
(a) a biological sample suspended in a collection medium comprising about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide;
(b) a first antibody; and
(c) a second antibody.

In an aspect, the disclosure provides for a composition comprising
(a) a biological sample suspended in a collection medium comprising about 0.5% to about 2.0% NP-40, about 0.10% to about 0.40% sodium deoxycholate, about 25 mM to about 75mM Tris-HCl, about 10 mM to about 50 mM EDTA, about 50 mM to about 200 mM NaCl, and about 0.01% to about 0.10% sodium azide;
(b) at least or one or more polynucleotide probes;
(c) a first antibody; and
(d) a second antibody.

In an aspect, the disclosure provides for a composition comprising
(a) a biological sample suspended in a collection medium, wherein the collection medium comprises at least one detergent;
(b) a denaturation reagent;
(c) at least one polynucleotide probe capable of binding to a target nucleic acid molecule;
(d) a support coated with a first antibody; and
(e) a second antibody labeled with a detectable marker.

In an aspect, any of the above compositions may be used may be used with any of the collection mediums described herein.

In an aspect, the biological sample in the above compositions is a cervical cell sample or a human cervical cell sample. In another aspect, the nucleic acid molecules in the biological sample are denatured. The biological sample in the above compositions can exhibit stability when stored in the collection medium for at least 21 days at 33° C. In an aspect, the second antibody is labeled with a detectable marker.

Biological Sample

Methods of the present invention may be used to detect the presence of a target nucleic acid molecule from samples, including, without limitation, a specimen or culture (e.g., cellular, microbiological and viral cultures) including biological and environmental samples. Biological samples may be from an animal, including a human, fluid, solid (e.g., stool) or tissue, as well as liquid and solid food and feed products and ingredients such as dairy items, vegetables, meat and meat by-products, and waste. Environmental samples include environmental material such as surface matter, soil, water and industrial samples, as well as samples obtained from food and dairy processing instruments, apparatus, equipment, utensils, disposable and non-disposable items.

Particularly preferred are biological samples including, but not limited to, cervical epithelial cells (e.g., a sample obtained from a cervical swab), adenoid cells, anal epithelial cells, blood, saliva, cerebral spinal fluid, pleural fluid, milk, lymph, sputum and semen. The sample may comprise a double-stranded nucleic acid molecule or may comprise a single-stranded nucleic acid molecule. If a double-stranded nucleic acid molecule is present, it may be prepared for hybridization analysis by a variety of methods known in the art, e.g., using alkali, using proteinase K/SDS, chaotropic salts. The process of preparing a double-stranded nucleic acid molecule for hybridization analysis generally involves converting it into a single-stranded nucleic acid molecule. This process is generally known as denaturation. However, it is also contemplated that a double-stranded nucleic acid molecule may be detected without denaturation, e.g., through a triple-stranded construct.

The target nucleic acid molecule in a sample can be DNA or RNA or both DNA and RNA. The target nucleic acid molecule can be contained within a larger nucleic acid molecule. Detection of either the target nucleic acid molecule or the larger nucleic acid molecule containing the target nucleic acid molecule is contemplated by this disclosure.

The biological sample may comprise cervical cells, especially human cervical cells. The sample can be collected with any method or device known in the art, including a chemically inert collection device such as a DACRON tipped swab. Other acceptable collection devices may be used including, but not limited to, cotton swab, cervical brush, flocked swab (a swab shaped like a DACRON swab but made with nylon fibers enabling collection of more cells and easier release of cells), cervical broom, mini broom, lavage, or any collection device often used in Pap smear testing.

In an aspect, the methods include collecting a sample from a woman over 30 years of age. The method can also include collecting a sample from a woman over 30 years via a Pap smear or comparable test. The sample collected by the Pap smear or comparable test can be a cervical cell sample.

Once the sample is collected, it may be placed in a sample tube. The tube can be sealed to prevent contamination. The collection device (swab, brush, etc.) may further contain a mechanism by which it can be moved once it is inside the sample tube. In one aspect, the collection device contains an insert that can be moved using a magnet. In one aspect, this insert comprises a metal. In another aspect, this insert comprises a magnetic material. Magnetic material includes paramagnetic, ferromagnetic, and diamagnetic materials. One advantage of moving the collection device once it is inside the sample tube is to avoid the collection device from making contact with any sample extraction or sample detection devices. Examples of a sample extraction device include pipettes, pipette tips, dropper bottles or other low tech extraction devices. Examples of sample detection devices include probes and probe tips.

The speed of this assay is also beneficial in screening samples from patients in remote living areas. Often patients will travel quite a distance to visit the doctor or clinic and will not likely return for some time thereafter. Thus, it is desirable to be able to test the patient and provide results while the patient waits at the clinic. In some circumstances, tracking down the patient to provide test results and/or treat the patient after they have left the doctor's office may be difficult. Thus, the described assays provide results over a short time, for example, between about 2 hours to about 3 hours, between about 2 hours to about 4 hours, between about 3 hours to about 5 hours, between about 4 hours to about 8 hours, or between about 6 hours to about 12 hours. In another aspect, the described assays provide results in less than about 2 hours, less than about 2.5 hours, less than about 3 hours, less than about 3.5 hours, less than about 4 hours, less than about 4.5 hours, less than about 5 hours, less than about 8 hours, less than about 12 hours, and less than about 24 hours. Such a short turnaround time allows the doctor to provide the patient with the results and/or treatment the same day the patient is at the clinic.

Sample Tube

Any type of sample tube may be used. Advantageously, the sample tube may be closed or sealed to minimize contamination. The closure may be permanent or removable. Examples of removable closures include snap caps, screw caps, rubber septa, foil, and film. The closure may contain one or more openings or perforations, which when pierced may be resealable. One advantage of a closure that contains such openings or perforations is that the closure is not rendered ineffective when pierced by, for example, a sample extraction device or sample detection device. Once the sample extraction device or sample detection device is removed, the closure re-seals, thereby minimizing contamination.

Storage of the Biological Sample

Once the sample is in the sample tube, the sample may be stored by drying it with a substrate, or in a preservative medium, or both. Desiccation is accomplished by pressure drying or drying with chemicals. This removes most of the water and is suitable for long-term stability. Alternatively, the sample may be lyophilized (freeze-dried) with a substrate like trehalose to ensure stability of the sample.

Another possibility is that the sample may be stored by suspending in a preservative medium, known and apparent to one of skill in the art. The purpose of the preservative medium is to protect biological components that can degrade. For instance, the sample cells, the probe mixture, the antibody: bead complex used in the capture step, and the secondary antibody used in the detection step are all susceptible to degradation. A preservative medium at the initial step of collection ideally provides sample stability and integrity and can affect downstream steps in the process of nucleic acid capture and detection. In an aspect, the sample may be stored at room temperature, refrigerated, or frozen either prior to or after the addition of the preservative medium.

Collection Medium

In an aspect, the sample may be collected and stored in a collection medium. The collection medium has several functions including as a preservative medium to preserve nucleic acids and inhibit nucleases to prevent degradation of nucleic acids prior to analysis. In one aspect, the collection medium contains at least one detergent. In another aspect, the collection medium contains at least two detergents, at least three detergents, or at least four detergents. In an aspect, each of the detergents is different. In another aspect, the detergent-based collection medium comprises two different detergents, one which is able to control background signal and another detergent that improves magnetic bead behavior, for example, migration through a viscous sample. Because the detergent improves the bead behavior, the beads can be washed with a variety of less precise devices, such as a squirt bottle, and dropper bottle, without causing too much disruption of the beads. Such methodology may be advantageous for use in developing countries where funds or access to technologically advanced equipment, such as pipetting devices, may not be available.

Further, the present invention provides a robust assay that can support using less precise reagent delivery devices. The reagents in this assay were designed to be robust and withstand variability in reagent volume delivery. For example, the neutralization step of the assay utilizes a highly buffered pH neutral solution to bring the very basic pH of the reaction to the appropriate pH range for hybridization with very large volume tolerances.

The use of a detergent-based collection medium for use in the assay can include one or more detergents. In an aspect, heat is employed during the hybridization, capture, and detection steps of the assay. Even with detergent and the application of heat, antibodies used in the assay remain functional.

FIG. 1 demonstrates that a detergent-based collection medium greatly improves the ability to prevent magnetic bead loss and migration during handling as compared to standard collection mediums. The detergent-based collection medium may comprise, consist essentially of, or consist of one, two, three, or four or more detergents. Detergents are known in the art and may include, but are not limited to, cationic detergents such as but not limited to cetyl pyridinium bromide, cetyltrimethylammonium bromide (collectively known as cetrimonium compounds) and alkylbenzyldimethylammonium chlorides (collectively known as benzalkonium compounds), and alkyl-trimethyl-ammonium salts; anionic detergents such as, but not limited to, sodium dodecyl sulfate (SDS), and Sarkosyl; and non-denaturing detergents such as NP-40; and other detergents. NP-40 is also known as Tergitol-type NP-40, which is nonyl phenoxylpolyethoxylethanol. NP-40 is not powerful enough to break the nuclear membrane, but can break the plasma membrane. As such, it can be used to obtain the cytoplasmic contents of a cellular culture.

Other detergents and combination of detergents may be used, and advantageously their combination provides the ability to control background noise and improve magnetic bead behavior (when the solid support employed comprises magnetic beads). In certain aspects, one detergent is an anionic detergent and the second detergent is a nonanionic detergent. For example, in one aspect, the combination of non-ionic and anionic detergents helps to maintain low-background noise. In an aspect, a detergent-based collection medium comprises an anionic detergent such as sodium deoxycholate, which controls background noise and NP-40, which improves magnetic bead behavior.

The combination of these two types of detergents provides synergistic benefits beyond a simple combination of adding two detergents together: control of background noise, better bead behavior, and increased assay speed. The presence of these detergents (in the detergent-based collection medium) provides the ability to achieve faster assay results, but does not negatively impact the nucleic acid or capture antibody during downstream analytical steps.

In addition, the detergent-based collection medium improves removal of the specimen from the collection device as the sample is dissolved more easily. In addition, the detergent-based collection medium improves the homogeneity of the sample compared with other collection media such as but not limited to PRESERVCYT (uses a 40% methanol solution), STM (uses a chaotropic agent), and alcohol. The detergent-based collection medium also reduced sample viscosity after mixing (either manual or automated).

The concentration of NP-40 in the collection medium can range from about 0.5% to about 2.0%, from about 0.1% to about 1.0%, as well as any number within the recited ranges. In certain aspects, the NP-40 is present at a concentration from about 0.8% to about 1.5%; from about 0.9% to about 1.2% and in certain aspects is about 1.0%. In another aspect, the NP-40 is present at a concentration from about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%. The concentration of sodium deoxycholate in the collection medium can range from about 0.10% to about 0.40%, from about 0.20% to about 0.30%, as well as any number within the recited ranges. In one aspect, the concentration of sodium deoxycholate is about 0.10%, about 0.15%, about 0.20%, about 0.25%, about 0.30%, about 0.35%, or about 0.40%.

The detergent-based collection medium may comprise, consist essentially of, or consist of a buffer, two detergents, a chelator and a preservative. The buffer may be Tris-HCl in a concentration of from about 25 mM to about 75 mM; from about 30 mM to about 60 mM; from about 40 mM to about 50 mM, and from about 45 mM to about 55 mM as well as any number within the recited ranges. The buffer may also be Tris-HCl in a concentration of about 25 mM, about 30 mM, about 35 mM, about 40 mM, about 45 mM, about 50 mM, about 55 mM, about 60 mM, about 65 mM, about 70 mM, or about 75 mM.

Any preservative can be used and the choice can depend on factors such as desired functionality, minimization side-effects, cost, etc. Suitable preservatives include gentomycin, ProClin, dimersol, and sodium azide. The concentration of the preservatives in the collection medium depends on factors such as the type of preservative, its efficacy, its side-effects, etc. For example, for sodium azide, the concentration of sodium azide can range from about 0.01% to about 0.1%, from about 0.025% to about 0.075%, and from about 0.04% to about 0.06%, as well as any number within the recited ranges. The preservative, for example, sodium azide, can also be present at about 0.01%, about 0.02%, about 0.03%, about 0.04%, 0.05%, about 0.06%, about 0.07%, about 0.08%, about 0.09%, or about 0.10%.

In one aspect the detergent-based collection medium comprises, consists essentially of, or consists of 1.0% NP-40, 0.25% sodium deoxycholate, 50 mM Tris-HCl, 25 mM EDTA, 150 mM NaCl and 0.05% sodium azide. In another aspect the detergent-based collection medium comprises, consists essentially of, or consists of about 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide. In other aspects the detergent-based collection medium comprises, consists essentially of, or consists of about 0.8% to about 1.5% NP-40, about 0.20% to about 0.40% sodium deoxycholate, about 30 mM to about 60 mM Tris-HCl, about 20 mM to about 40 mM EDTA, about 100 mM to about 200 mM NaCl, and about 0.025% to about 0.075% sodium azide. In yet another aspect the detergent-based collection medium comprises, consists essentially of, or consists of about 0.9% to about 1.2% NP-40, about 0.20% to about 0.30% sodium deoxycholate, about 30 mM to about 60 mM Tris-HCl, about 20 mM to about 30 mM EDTA, about 100 mM to about 150 mM NaCl, and about 0.04% to about 0.06% sodium azide.

In an aspect, the collection medium comprises, consists essentially of, or consists of NP-40 and EDTA. In another aspect, the collection medium comprises, consists essentially of, or consists of NP-40, EDTA, and sodium azide. In one aspect, the collection medium comprises, consists essentially of, or consists of sodium deoxycholate, EDTA, and sodium azide. In an aspect, the collection medium comprises, consists essentially of, or consists of about NP-40, sodium deoxycholate, EDTA, and sodium azide. In an aspect, the collection medium comprises, consists essentially of, or consists of NP-40, sodium deoxycholate, Tris-HCl, EDTA, and sodium azide.

In another aspect, the collection medium comprises, consists essentially of, or consists of 0.5% to about 2.0% NP-40 and 10 mM to about 50 mM EDTA. In another aspect, the collection medium comprises, consists essentially of, or consists of 0.5% to about 2.0% NP-40, 10 mM to about 50 mM EDTA, and about 0.01% to about 0.10% sodium azide. In one aspect, the collection medium comprises, consists essentially of, or consists of about 0.10% to about 0.40% sodium deoxycholate, 10 mM to about 50 mM EDTA, and about 0.01% to about 0.10% sodium azide. In an aspect, the collection medium comprises, consists essentially of, or consists of about 0.5% to about 2.0% NP-40, about 0.10% to about 0.40% sodium deoxycholate, 10 mM to about 50 mM EDTA, and about 0.01% to about 0.10% sodium azide. In an aspect, the collection medium comprises, consists essentially of, or consists of about 0.5% to about 2.0% NP-40, about 0.10% to about 0.40% sodium deoxycholate, about 25 mM to about 75 mM Tris-HCl, about 10 mM to about 50 mM EDTA, and about 0.01% to about 0.10% sodium azide.

In an aspect, the collection medium is a non-chaotropic medium. That is, for example, the collection medium does not include a chaotropic medium or chaotropic salts. Without being limited, in an aspect, the collection medium does not include guanidine hydrochloride or urea. A potential advantage of using a non-chaoptropic collection medium is better resuspension of a sample, more reproducible testing, and more uniform testing aliquots relative to a medium which includes a chaotropic medium or chaotropic salts.

An advantage of using a detergent-based collection medium is that it preserves the stability of the sample. A sample stored in a detergent-based collection medium as disclosed is stable for at least 31 days, and, when held at temperatures from 15° C. to 33° C. is stable for at least 21 days. In an aspect, a sample is stable when frozen in a detergent-based collection medium at −20° C. for at least six months. In another aspect, a cervical cell sample is stable for at least 31 days, for at least 21 days when held at temperatures from 15° C. to 33° C., and for at least 6 months in a detergent-based collection medium at −20° C.

In an aspect, the detergent-based collection medium exhibits a sensitivity for detecting cervical intraepithelial neoplasia or cancer of at least 80%, at least 90%, or at least 95% for a cut-off ratio of 0.5 relative light units. In another aspect, the detergent-based collection medium exhibits a specificity for detecting cervical intraepithelial neoplasia or cancer of at least 80%, at least 90%, or at least 95% for a cut-off ratio of 0.5 relative light units. In yet another aspect, the detergent-based collection medium exhibits a sensitivity for detecting severe or moderate cervical intraepithelial neoplasia or cancer (CIN2+) of about 90% and a of specificity of about 84% for a cut-off ratio of 0.5 relative light units . In an aspect, the detergent-based medium includes 0.5% to about 2.0% NP-40, about 0.10% to about 0.40% sodium deoxycholate, about 25 mM to about 75 mM Tris-HCl, about 10 mM to about 50 mM EDTA, about 50 mM to about 200 mM NaCl, and about 0.01% to about 0.10% sodium azide.

A detergent-based collection medium also leads to improved assay performance under rigorous hybridization and capture conditions (for example, at temperatures between 65°-75° relative to collection medium containing a denaturant.

The presence of one, two, three, four or more detergents can reduce sample viscosity, which aids in the removal of the liquid phase from the magnetic beads, as well as aids in the mixing of samples.

In one aspect, a sample such as blood or an exfoliated cervical cell specimen can be collected and suspended in a detergent-based collection medium. The sample can be is collected with a chemically inert collection device such as a DACRON tipped swab. Any other suitable swab may be used such as nylon fiber swabs. The sample may be stored in a detergent-based collection medium, to prevent degradation of nucleic acids prior to analysis and to maintain stability of the sample.

Samples may be collected in other known collection mediums and then can be used in the methods described herein. Examples of other collection media include PRESERVCYT, SUREPATH, DCM (DIGENE Collection Medium), and STM (Sample/Specimen Transport Medium). Certain collection media are nucleic acid specific. For example DCM is not used when the target nucleic acid is RNA. Samples collected in some of these media may require processing before the nucleic acids in the samples can be detected and analyzed. Various methods of processing samples (also known as preparing the samples) are known in the art. For example, cervical cell samples collected for cytological analysis in medium such as PRESERVCYT may be combined with a detergent-based lysis buffer followed by the addition of magnetic beads comprising nucleic acid binding surfaces. In addition, other cell samples collected in other known commonly available collection mediums may be combined with a detergent-based lysis buffer followed by the addition of magnetic beads comprising nucleic acid binding surfaces.

Target Nucleic Acid Molecules

The target nucleic acid molecules include, without limitation, nucleic acid molecules found in specimens or cultures (e.g., cellular, microbiological and viral cultures) including biological and environmental samples. The target nucleic acid molecules may be found in biological samples from an animal, including a human, fluid, solid (e.g., stool) or tissue, as well as liquid and solid food and feed products and ingredients such as dairy items, vegetables, meat and meat by-products, and waste. Target nucleic acid molecules may be found in environmental samples and include environmental material such as surface matter, soil, water and industrial samples, as well as samples obtained from food and dairy processing instruments, apparatus, equipment, utensils, disposable and non-disposable items.

The target nucleic acid molecules found in biological samples include, but not limited to cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen. The target nucleic acid molecules may be from other viral, bacteria, mycobacteria or plasmodia, for example cytomegalovirus (CMV), herpes, HIV, H1N1, chlamydia, gonorrhea, *Trichomonas vaginalis, Staphylococcus aureus*, tuberculosis, SARS-associated coronavirus or influenza. In an aspect the target nucleic acid molecules are at least 70%, at least 80%, at least 85%, at least 90%, at least 95%, at least 96%, at least 97%, at least 98%, at least 98%, at least 99%, or 100% identical to nucleic acid molecules associated with any one of cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen, other viral, bacteria, mycobacteria or plasmodia, for example cytomegalovirus (CMV), herpes, HIV, H1N1, *chlamydia, gonorrhea, Neis-* seria gonorrhoeae (GC), *Chlamydia trachomatis* (CT), *Trichomonas vaginalis, Staphylococcus aureus*, tuberculosis, SARS-associated coronavirus or influenza.

In one aspect, the target nucleic acid molecules are human papillomavirus (HPV) and include genetic variants of HPV. A variant includes polymorphisms, mutants, derivatives, modified, altered, or the like forms of the target nucleic acid. In one aspect, the target nucleic acid is an HPV nucleic acid. In another aspect, the HPV nucleic acid is HPV DNA of a high risk HPV type. In another aspect, the HPV nucleic acid is HPV RNA of a high risk HPV type. In another aspect the target nucleic acids are any one of high risk HPV types 16, 18, 26, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83.

In another aspect, the target nucleic acid molecule is at least 70%, at least 80%, at least 85%, at least 90%, at least 95%, at least 96%, at least 97%, at least 98%, at least 98%, at least 99%, or 100% identical to nucleic acid molecules associated with any one of HPV, genetic variants of HPV, HPV DNA of a high risk HPV type, or HPV RNA of a high risk HPV type. In another aspect the target nucleic acids are at least 70%, at least 80%, at least 85%, at least 90%, at least 95%, at least 96%, at least 97%, at least 98%, at least 98%, at least 99%, or 100% identical to nucleic acid molecules associated with any one of high risk HPV types 16, 18, 26, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83.

Figure 2:
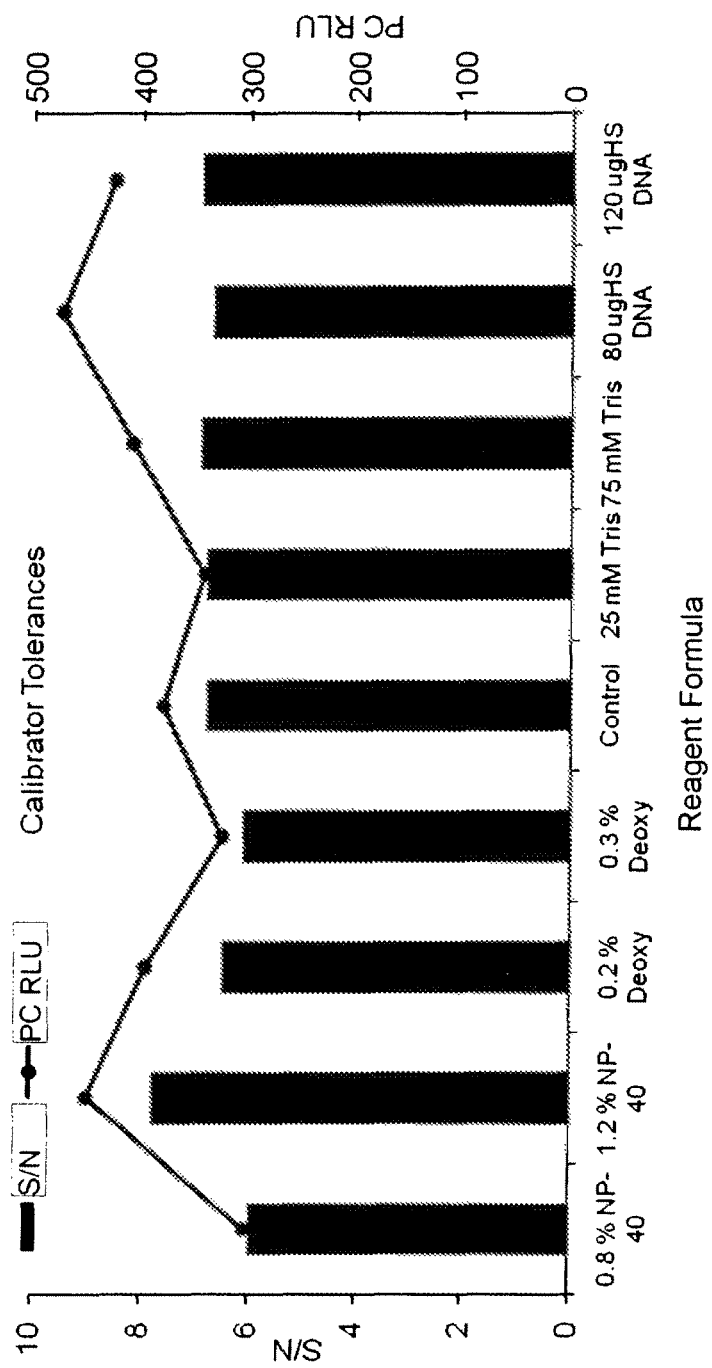
FIG. 2 shows that samples having only 0.2 pg target nucleic acid (DNA) per ml of sample provide a readable signal using methods of the present invention.

Using methods of the present inventions, the target nucleic acid molecule may be present at concentrations less than about 1 pg per ml, less than about 0.75 pg per ml, less than 0.5 pg per ml, less than 0.25 pg per ml, and even as low as 0.2 pg per ml. As seen in FIG. 2 an excellent signal to noise ratio is obtained when HPV-16 DNA was used as the target nucleic acid molecule present at a concentration of 0.2 pg per ml.

As noted previously, the target nucleic acid molecule may be DNA or RNA. When the target nucleic acid molecule is DNA, the probe is preferably RNA and when the target nucleic acid is RNA, the probe is preferably DNA. However, a DNA probe can be used with DNA target nucleic acid molecule and an RNA probe can be used with RNA target nucleic acid molecule. Also as indicated previously, the target nucleic acid molecule may determine the collection medium used.

Denaturation

After the sample is collected in a detergent-based collection medium as described above, the sample may be treated with a denaturation reagent to render the target nucleic acid molecule accessible to hybridization. In one aspect, the sample is denatured with an alkaline solution. Any alkali that can bring a solution pH to about pH 12, about pH 13, or about pH 14 may be used. Additionally, any alkali that can bring a solution pH to a range of about pH 12 to about pH 13, from about pH 12 to about pH 14, and from about pH 13 to about pH 14 can be used. Suitable concentrations of alkali include from about 1.0 N to about 2.0 N, from about 1.25 N to about 1.75 N, and from about 1.25 N to about 1.5 N, and about 1.5 N as well as any number within the recited ranges. Without being limited, suitable alkali include NaOH and KOH.

In one example, approximately one volume of the sample suspended in a detergent-based collection medium can be treated with about one-half volume of 1.75 N NaOH solution. For example, in certain aspects approximately a 50 µl aliquot is removed from a sample suspended in a detergent-based collection medium and approximately 25 µl of 1.75 N NaOH solution is added to the 50 µl aliquot sample. At room temperature, the sample treated with the denaturation reagent can be mixed by hand mixing or mechanical shaking at about 800 rpm, about 900 rpm, about 1000 rpm, between about 600 and about 1000 rpm, or between about 600 and 1200 rpm. The pH of the sample after addition of denaturation reagent can be about 14. In another aspect, the pH can be about pH 12 or pH 13. Such basic pH will both nick and denature a majority of the nucleic acid in the specimen. In addition, alkaline treatment can disrupt interactions between peptides and nucleic acids to improve accessibility of the target nucleic acid and degrade protein.

Alkaline treatment of protein effectively homogenizes the specimen to ensure reproducibility of analysis results for a given sample. It can also reduce the viscosity of the sample to increase kinetics, homogenize the sample, and reduce background by destroying any endogenous single stranded RNA nucleic acids, DNA-RNA hybrids or RNA-RNA hybrids in the sample. It also helps inactivate enzymes such as RNases and DNases that may be present in the sample. One skilled in that art would appreciate that if RNA is the target nucleic acid (as opposed to DNA), different reagents may be preferable including, but not limited to phenol extraction and TCA/acetone precipitation, and guanidinium thiocyanate-phenol-chloroform extraction.

Other methods of denaturation may be employed such as utilizing a heating step, for example, heating the sample to about 95° C. to separate the strands of nucleic acid. Enzymes such as helicase may be used as well.

In one aspect, 1.5 N to 2.0 N NaOH is added to the sample and heated. In another aspect, 1.75 N NaOH is added to the sample and heated. The sample with denaturation reagent may be heated to about 60° C. to about 80° C. for about 30 minutes, to about 65° C. to about 75° C. for about 30 minutes, to about 67° C. to about 70° C. for about 30 minutes, or to about 70° C. for about 30 minutes, or any number within the recited ranges. In another aspect, the sample with denaturation reagent is heated to about 60° C. to about 80° C. for about 20 to about 40 minutes, or to about 65° C. to about 75° C. for about 20 to about 40 minutes, to about 67° C. to about 70° C. for about 20 to about 40 minutes, or to about 70° C. for about 20 to about 40 minutes, or any number within the recited ranges. The goal of the described time and temperature conditions is to provide for maximal denaturation of the sample in a minimum amount of time, while leaving the target nucleic acid in a suitable condition for carrying out the remaining steps of hybridization, capture, washing, and detection. Therefore, the sample may be heated in denaturation reagent for about 5 to about 120 minutes, about 10 to about 60 minutes, about 20 minutes to about 40 minutes, about 30 minutes, or any number within the recited ranges. It will be readily understood by one of ordinary skill in the art that longer periods of incubation at lower temperatures, or shorter periods of incubation at higher temperatures, may be balanced to provide a similar effect to the conditions described herein.

Hybridization and Binding of Probes

After the sample containing the nucleic acid is denatured, it is contacted with one or more polynucleotide probes under a condition sufficient for the one or more polynucleotide probes to hybridize to the target nucleic acid in the sample to form a double-stranded nucleic acid hybrid. The probe can be full length, truncated, or synthetic DNA or full length, truncated, or synthetic RNA. If the target nucleic acid is DNA, then the probe may be RNA and if the target nucleic acid is RNA, then the probe may be DNA. Preferably, the one or more polynucleotide probes are diluted in a probe diluent that also can act as a neutralizing hybridization buffer (to neutralize the basic denaturation reagent).

The probe diluent used for DNA or RNA probes will differ due to the different requirements necessary for DNA versus RNA stability. For example, if the probes are RNA, it is preferable to neutralize the sample first and than add the probe or alternatively, add the RNA probe and neutralizing agent (probe diluent) to the sample at the same time as NaOH can destroy RNA. The probe diluent can be used to dissolve and dilute the probe and also help restore the sample to about a neutral pH, e.g., about pH 6 to about pH 9, to provide a more favorable environment for hybridization. Sufficient volume of probe diluent, preferably one-half volume of the sample, may be used to neutralize the base-treated sample.

In an aspect, the probe diluent comprises a buffer, polyacrylic acid, NaOH and sodium azide. The probe diluent may comprise acetic acid. In one aspect, the probe diluent comprises 2.2 M BES (N,N-Bis(2-hydroxyethyl)-2-aminoethanesulfonic acid), 2.6% polyacrylic acid (PAA), 0.7 N NaOH and 0.05% sodium azide. The probe diluent may contain from about 1.2 M to about 2.6 M BES, from about 1.5 M to about 2.5 M BES; from about 1.75 M to about 2.25 M BES; from about 2 M to 2.4 M BES, or about 2.2 M BES, as well as any number within the recited ranges. In one aspect the probe diluent may contain from about 2% to about 3.0% PAA or, as well as any number within the recited ranges. In another aspect, the PAA concentration is from about 2.2% to about 2.7%. In yet another aspect, the PAA concentration is about 2.6%. In a further aspect the probe diluent may contain from about 0.6 N to about 0.8 N NaOH, for example, about 0.7 N NaOH. The concentration of NaOH generally increases as the amount of BES increases.

For full length probes, a heated alkaline solution may be added to the sample, then probe diluent may be added to the sample at room temperature, and then the sample may be reheated. Such a process can inhibit secondary structure from forming. Antibodies tend to irreversibly bind to structures with secondary structure. When using non-full length probes such as truncated or synthetic probes, heating the solutions or sample may not be necessary because secondary structures issues are not present. In an aspect, the sample is not heated when used with truncated or synthetic probes.

After treatment with the denaturation reagent, an aliquot of neutralization buffer, in an aspect the probe diluent described, in which the one or more probes are dissolved, can be added to the sample under appropriate conditions to allow hybridization or binding of the probe and the target nucleic acid to occur. The neutralization buffer may contain a single buffering salt. In an aspect, the neutralization buffer does not contain more than a single buffering salt. The hybridization condition is sufficient to allow the one or more polynucleotide probes to anneal to a corresponding complementary nucleic acid sequence, if present, in the sample to form a double-stranded nucleic acid hybrid.

Hybridization conditions suitable for the particular probes and diluents described herein are employed. For example, the probes and sample nucleic acids can be incubated for a hybridization time, preferably at least about 5 to about 30 minutes, about 5 to about 20 minutes, or from about 7 to about 15 minutes, or about 10 minutes, as well as any number within the recited ranges sufficient to allow the one or more polynucleotide probes to anneal to a corresponding complementary nucleic acid sequence. The hybridization condition can include a hybridization temperature of at least about 65° C., about 68.5° C., and about 67° C. to about 70° C., as well as any number within the recited ranges. For a given target nucleic acid and a given probe, one of ordinary skill in the art can readily determine desired hybridization conditions by routine experimentation. One of ordinary skill in the art will further appreciate that the time and temperature of hybridization must be optimized, one with respect to the other. Thus, higher hybridization temperatures may be carried out for shorter periods of time and vice versa. Without being limited, stringent hybridization conditions may be controlled by increasing the temperature, increasing the ionic conditions to above 0.5 M (for example, NaCl), or reducing the concentration of PAA. As a non-limiting example, stringent hybridization conditions may include performing a hybridization reaction at elevated temperatures, such as of at least about 65° C., at least about 68.5° C., between about 67° C. to about 70° C. , and between about 69° C. to about 70° C. Stringent hybridization conditions may also include elevated temperatures, such as of at least about 65° C., at least about 68.5° C., and between about 67° C. to about 70° C.

In a non-limiting aspect, the probe is capable of hybridizing or binding to nucleic acid molecules at least 70%, at least 80%, at least 85%, at least 90%, at least 95%, at least 96%, at least 97%, at least 98%, at least 98%, at least 99%, or 100% identical to nucleic acid molecules associated with HPV, genetic variants of HPV, HPV DNA of a high risk HPV type, or HPV RNA of a high risk HPV type, or any one of high risk HPV types 16, 18, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83. In another aspect, the probe is complementary to HPV, genetic variants of HPV, HPV DNA of a high risk HPV type, HPV RNA of a high risk HPV type, or any one of high risk HPV types 16, 18, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83.

In one aspect, the sample is suspended in detergent-based collection medium, the target nucleic acid is denatured with a denaturation reagent, and hybridized to nucleic acid probes suspended in a neutralizing buffer. In another aspect the neutralizing buffer is the probe diluent of the present invention. The probe diluent can comprises 2.2 M BES (N,N-bis(2-hydroxyethyl)-2-aminoethanesulfonic acid), 2.6% polyacrylic acid, 0.7 N NaOH and 0.05% sodium azide.

Capture

After the probes are allowed to hybridize to the target nucleic acid molecule and to form a double-stranded nucleic acid hybrid, the hybrid is captured by a molecule that is specific for the double-stranded nucleic acid hybrid. Molecules specific for the double stranded nucleic acid hybrids include, but are not limited to, monoclonal antibodies, polyclonal antibodies, proteins such as but not limited to RNAse H, nucleic acids including but not limited to aptamers, or sequence specific nucleic acids. Aptamers are short stretches of random sequences that are successively selected from a library of sequences by hybridizing to a target, amplifying the hybridized aptamers, and repeating the selection process. In one aspect the molecule specific for the double stranded nucleic acid hybrid is captured by an antibody, known as an anti-hybrid antibody.

In one aspect, a first anti-hybrid antibody is immobilized onto a support using techniques that are standard in the art. Examples of suitable supports include covalent linkages or adsorption, for example, protein-protein interactions, protein-G beads, biotin-streptavidin interaction, EDAC to link to a carboxyl or tosyl group, etc., or hybridization directly onto the solid support using, for example, sequence specific nucleic acids in an affinity column.

Supports include but are not limited to beads, magnetic beads, which as indicated previously include paramagnetic, diamagnetic, ferromagnetic, ferromagnetic, and diamagnetic beads, columns, plates, filter paper, polydimethylsiloxane (PDMS), and dipsticks. Any support can be used as long as it allows extraction of the liquid phase and provides the ability to separate out bound and unbound antibodies. Magnetic beads are particularly useful in that they can be left in the solution and the liquid phase can be extracted or decanted, if a magnetic field is applied to immobilize the beads. Beads that are small and have a high surface area are preferable, such as beads about 1 μm in diameter. Other beads that employ charge switching or silica capture (as opposed to magnetic fields) may be used as well.

The hybrids are incubated with the anti-hybrid antibody attached to the support for a sufficient amount of time to allow capture of the double-stranded nucleic acid hybrids by the immobilized anti-hybrid antibodies. In an aspect, the support is a bead.

The anti-hybrid antibody may be monoclonal or polyclonal. In one aspect the antibody is monoclonal. In one aspect, the antibody is coupled to support by an 1-ethyl-3-[3-dimethylaminopropyl] carbodiimide hydrochloride (EDAC) linker. In one aspect, the support is a polystyrene bead. In an aspect, the support or bead coupled to the antibody is diluted in a bead dilution buffer. The bead dilution buffer is helpful in minimizing protein denaturation on the bead. One example of a bead dilution buffer comprises 6% casein, 100 mM Tris-HCl, 300 mM NaCl, and 0.05% sodium azide.

In an aspect, the beads coated with the anti-hybrid antibody are incubated with the sample at about 67° C. to about 70° C. for about 30 minutes. In another aspect, the beads and sample are incubated at about 68° C. to about 69° C. for about 30 minutes. In yet another aspect, the beads and sample are incubated at about 68.5° C. for 30 minutes. The incubation time can range from about 5 minutes to about 60 minutes, from about 15 minutes to about 45 minutes, from about 20 minutes to about 40 minutes, or any number within the recited ranges, and is generally inversely proportional to the temperature. It will be understood by those skilled in the art that the incubation time, temperature and/or shaking conditions can be varied to achieve alternative capture kinetics as desired.

Following capture of the target nucleic acid/probe hybrid as described above, the captured hybrid may be separated from the rest of the sample by washing away of non-captured nucleic acids.

Conjugation

Another step in the method can involve providing a second antibody that is also specific for double stranded nucleic acids hybrids or alternatively is specific for the first antibody. The second antibody may be detectably labeled, either directly or indirectly, and may be a monoclonal or polyclonal antibody. In an aspect, the second antibody is monoclonal. In another aspect, the second antibody is directly labeled with a detectable marker and is monoclonal. The second antibody is used to detect the presence of double-stranded nucleic acid hybrids. In one aspect, the second antibody has a label that must react with a substrate to provide a signal that can be detected. The second antibody may be dissolved in a suitable buffer. In one aspect the buffer comprises 100 mM TrisHCl, pH 7.4, 0.5 M NaCl, 0.1 mM $ZnCl_2$, 1.0 mM $MgCl_2$, 0.25% Tween 20, 0.2 mg/ml RNase A, 4% hydroxypropyl-b-cyclodextrin (cyclodextrin), 30% bead dilution buffer as discussed previously, 0.05% goat IgG, 0.05% sodium azide.

In an aspect, the conjugation reaction takes place at room temperature. In an aspect, the conjugation reaction takes place at room temperature for between about 1 hour and 2 hours. In another aspect, the conjugation reaction takes place at room temperature for about 2 hours. In another aspect the conjugation reaction takes place at about 37° C., about 45° C., or about 50° C. In an aspect the conjugation reaction takes place at about 37° C., about 45° C., or about 50° C., between 35° C. and about 40° C., between 40° C. and about 50° C. for between about 20 minutes and 40 minutes. In an aspect the conjugation reaction takes place at about 37° C., about 45° C., or about 50° C. for between about 20 minutes and 40 minutes. In another aspect the conjugation reaction takes place at about 45° C. for about 30 minutes.

It will be understood by those skilled in the art that any detectable label such as, but not limited to, an enzyme, radioactive molecule, fluorescent molecule, or metal particle such as gold particle can be used. In certain aspects, the detectable label is alkaline phosphatase. Methods of conjugating a label to an antibody are known. For example, an antibody can be reduced with dithiothreitol (DTT) to yield monovalent antibody fragments. The reduced antibody can then be directly conjugated to maleinated alkaline phosphatase by the methods of Ishikawa et al., J. Immunoassay 4:209-237 (1983) and Means et al., Chem. 1: 2-12 (1990), the contents of each of which are incorporated herein by reference in its entirety, and the resulting conjugate can be purified by HPLC. The conjugate may also be purified using any type of size-exclusion chromatography. One benefit of purification is that the conjugates of one protein to one antibody can be separated from those conjugates with other ratios of protein to antibody.

In another aspect, the double-stranded nucleic acid hybrids can be detected with a second anti-hybrid antibody that is not directly labeled. For example, the second antibody can be a mouse immunoglobulin that is detected by a labeled goat anti-mouse antibody.

Wash

Following conjugation with the second antibody, the sample is washed with a based wash buffer. The wash buffer may contain one or more detergents or may be free of a detergent. If the wash buffer contains a detergent, the detergent may be an ionic or a non-ionic detergent. One example of a non-ionic detergent is Triton-X. The detergent may be present in the wash buffer at a concentration of about 0.05% to about 1.5%, or from about 0.075% to about 1.0%, or from about 0.1% to about 0.75%, or about 0.5% or any number within the recited ranges. One example of a suitable wash buffer comprises 40 mM Tris, pH 8.2, 100 mM NaCl, 0.5% Triton-X 100 and 0.05% sodium azide.

The sample may be washed with the wash buffer from one to ten times, or from three to seven times, or from four to six times, or five times, or any number within the recited ranges. The sample may also be washed with a single wash buffer or with multiple wash buffers. Each wash may use the same wash buffer or a different wash buffer. For example, a detergent-containing wash buffer may be used for one wash while a detergent-free wash buffer may be used for another wash. In an aspect, one of the wash buffers does not include Triton.

One benefit of the detergent-containing wash buffer is the positive effects on bead behavior when compared to detergent-free wash buffers. The detergent-containing wash buffer allows for rapid, efficient, and resilient binding of the beads to the magnetic field. Binding of the beads to the magnetic field is strong enough that beads remain bound through physical inversion and decanting. While detergent-free wash buffers generally do not allow for physical inversion without bead loss, they may be used for other purposes. One example of the use of a detergent-free wash buffer is to remove or dilute a detergent in the sample thereby reducing any likely detection problems.

Detection

The label present on the second, or third, or more, antibody is detected to thus indicate the presence of the target nucleic acid molecule. Methods for detecting various labels are known in the art. For example, colorimetry, radioactive, surface plasmon resonance, or chemiluminescence methods are described by e.g., Coutlee et al., J. Clin. Microbiol. 27:1002-1007 (1989), the contents of which are incorporated herein by reference in its entirety.

For example, a bound alkaline phosphatase conjugate can be detected by chemiluminescence with a reagent such as a LUMI-PHOS 530 reagent (Lumigen, Detroit, Mich.) or DR2 (Applied Biosystems, Foster City, Calif.) using a detector such as an E/LUMINA luminometer (Source Scientific Systems, Inc., Garden Grove, Calif.), an OPTOCOMP I Luminometer (MGM Instruments, Hamden, Conn.), or the like, such as a Veritas Microplate Luminometer by Turner Biosystems. Multiple detection techniques can also be used in sequence or in parallel. For example, the conjugate may be detected by chemiluminescence and fluorescence. In another aspect, the conjugate can be detected by chemiluminescence.

Detectors using different detection techniques for the conjugate may be reversible or irreversibly attached, for example in a modular fashion, to a machine that is capable of performing the method for determining the presence of a target nucleic acid molecule in a sample.

As described herein, detection of the label on the second antibody is indicative of the presence of one or more of the target nucleic acid molecules in the sample that are complementary to the one or more probes. Following washing, the sample is suspended in a detection buffer that for example, contains the substrate for the label on the second antibody.

In one aspect, the sample is comprised of cervical cells. The method for determining the presence of a target nucleic acid molecule in a sample of cervical cells comprises suspending the sample in a detergent-based collection medium and mixing by hand mixing. In another aspect the mixing is mechanical. An approximately 50 µl aliquot of the sample is removed and mixed with about 25 µl of a denaturation reagent. The sample is mixed by hand mixing or mechanical shaking at between about 600 to about 1200 rpm for about 30 to about 60 seconds and heated at about 70° C. for about 30 minutes. High risk HPV RNA probes are prepared in a diluent and diluted to about 375 ng/ml. About 40 µl of diluted probe is added to the sample on a 70° C. heating block. The samples are further incubated at approximately 68.5° C. with shaking at about 1150 rpm for about 30 minutes. The supernatant can be removed by a dropper bottle or other low tech device. About 35 µl of the detection reagent is added to the sample. The detection reagent contains a second antibody that is labeled. The second antibody is specific for double-stranded nucleic acid hybrids. The sample containing the detection reagent is incubated at about 45° C. for about 30 minutes, placed on a magnetic rack for about 30 seconds to 3 minutes and the supernatant is decanted. In another aspect the sample containing the detection reagent is incubated at room temperature. The sample is then washed with wash buffer about four or five times.

Anti-hybrid Antibodies

The double-stranded nucleic acid hybrids formed in accordance with the present invention can be captured and detected using antibodies that are specific to double-stranded nucleic acid hybrids. The antibody is specific to double-stranded hybrids, such as but not limited to RNA-DNA; DNA-DNA; RNA-RNA; and mimics thereof, where mimics refer to molecules that behave similarly to RNA-DNA, DNA-DNA, or RNA-RNA hybrids. The anti-double-stranded nucleic acid hybrid antibody, i.e., the anti-hybrid antibody that is utilized will depend on the type of double-stranded nucleic acid hybrid formed. In one aspect, the anti-hybrid antibody is immunospecific to RNA-DNA hybrids.

It will be understood by those skilled in the art that either polyclonal or monoclonal anti-hybrid antibodies can be used and/or coupled to beads and/or immobilized on a support in the present assay as described below. Monoclonal antibody prepared using standard techniques can be used in place of the polyclonal antibodies. Monoclonal antibodies may be produced by methods that are standard in the art. In an aspect, the antibodies used for capture and detection of the target nucleic acid are monoclonal antibodies. In an aspect, monoclonal antibodies support high stringency incubation temperatures during the capture step. Without being limited, the high stringency incubation temperatures during the capture step may be between about 65° to about 75° C. or between about 68° to about 75° C. The first and second antibodies may be the same for capture and detection (i.e., produced by the same hybrid myeloma cell line) or may be different and produced by different hybrid myeloma cell lines. In one aspect, the first and second monoclonal antibodies used for capture and/or detection are the same and are specific for RNA-DNA hybrids. Also included are immunofragments or derivatives of antibodies specific for double-stranded hybrids, where such fragments or derivatives contain binding regions of the antibody.

For example, a monoclonal anti-RNA-DNA hybrid antibody derived from myeloma cells fused to spleen cells that are immunized with an RNA-DNA hybrid can be used. The hybrid-specific antibody can be purified by affinity purification against RNA-DNA hybrids immobilized on a solid support, for example as described in Kitawaga et al., Mol. Immunology, 19:413 (1982); and U.S. Pat. No. 4,732, 847, the contents of each of which are incorporated herein by reference in their entirety.

Other suitable methods of producing or isolating antibodies, including human or artificial antibodies, can be used, including, for example, methods that select recombinant antibody (e.g., single chain $F_v$ or $F_{ab}$, or other fragments thereof) from a library, or which rely upon immunization of transgenic animals (e.g., mice) capable of producing a repertoire of human antibodies (see, e.g., Jakobovits et al., Proc. Natl. Acad. Sci. USA, 90:2551 (1993); Jakobovits et al., Nature, 362: 255 (1993); and U.S. Pat. No. 5,545,806 and U.S. Pat. No. 5,545, 807, the contents of each of which are incorporated herein by reference in their entirety).

In one aspect, the target nucleic acid to be detected is DNA (e.g., HPV genomic DNA or cDNA) or RNA (e.g., mRNA, ribosomal RNA, nuclear RNA, transfer RNA, viral RNA, heterogeneous nuclear RNA), wherein the one or more polynucleotide probes are polyribonucleotides or polydeoxyribonucleotides, respectively. In a preferred aspect, the double-stranded nucleic acid hybrids are DNA-RNA hybrids formed by hybridization of target DNA and probe RNA, and can be detected using an antibody that is immunospecific to RNA-DNA hybrids.

In an aspect of the present invention, a monoclonal anti-RNA-DNA hybrid antibody derived from a hybridoma cell line is used. Such hybridoma cell lines are described in U.S. Pat. No. 4,865,980, U.S. Pat. No. 4,732,847, and U.S. Pat. No. 4,743,535, the contents of each of which are incorporated herein by reference in their entirety. Hybrid-specific monoclonal antibodies may be prepared using techniques that are standard in the art. The hybrid-specific monoclonal antibody may be used for both capturing and detecting the target nucleic acid.

While any vertebrate may be used for the preparation of polyclonal anti-RNA-DNA hybrid antibodies, goats or rabbits are preferred. Preferably, a goat or rabbit is immunized with a synthetic poly(A)-poly(dT) hybrid by injecting the hybrid into the animal in accordance with conventional injection procedures. Polyclonal antibodies may be collected and purified from the blood of the animal with antibodies specific for the species of the immunized animal in accordance with well-known antibody isolation techniques. For the production of monoclonal antibodies, the spleen can be removed from the animal after a sufficient amount of time, and splenocytes can be fused with the appropriate myeloma cells to produce hybridomas. Hybridomas can then be screened for the ability to secrete the anti-hybrid antibody. Selected hybridomas may then be used for injection into the peritoneal cavity of a second animal for production of ascites fluid, which may be extracted and used as an enriched source of the desired monoclonal antibodies incorporated herein by reference.

Polynucleotide Probes

The polynucleotide probes are designed to hybridize or bind with the target nucleic acid molecules. In another aspect, the polynucleotide probes are designed to bind to target nucleic acid molecules. In one aspect, the probes are capable of hybridizing or binding to HPV and HPV high risk variants. In an additional aspect, the polynucleotide probes are specific for HPV and HPV high risk variants. High risk (HR) nucleic acid probes can include probes for HPV high risk types 16, 18, 31, 33, 35, 39, 45, 51, 52, 56, 58, 59, 66, 68 and 82. In other aspects the RNA or DNA probes are fragments. In an aspect, the probes are about 6 to about 8 kilobases in length, preferably about 7.5 kilobases, and may be produced using a plasmid template using a BLUESCRIPT vector. However, other plasmids, vectors and methods are known in the art and could also be used to produce the RNA probes described herein.

The probes may vary in amount from about 7.5 ng to about 60 ng per HPV type per assay, or from about 20 ng to about 45 ng per HPV type per assay, or about 30 ng of probe for each HPV type per assay is used. Thus, in one aspect the HR probes consist of or consist essentially of one or more probes for HPV high risk types 16, 18, 31, 33, 35, 39, 45, 51, 52, 56, 58, 59, 66, 68, and 82 or low risk HPV types 6, 11, 40, 43, 53, 61, 67, 69, 70, 71, 72, 81, and 83, wherein about 30 ng of each probe is used per assay for detection of the target nucleic acid molecule.

The RNA probes may be short synthetic RNA probes that specifically bind only to the target nucleic acid molecule. Examples are described in U.S. patent application Ser. No. 12/426,076, filed on Apr. 17, 2009, the contents of which are incorporated herein by reference in its entirety.

Cross-Reactivity

The present invention also provides for assay compositions, probes, and conditions wherein cross-reactivity between HPV HR probe sets and low risk HPV types is dramatically reduced when compared to the standard FDA approved HPV assay and probe set. In one aspect, the HPV HR probe set is selected from the group consisting of HPV high risk types 16, 18, 31, 33, 35, 39, 45, 51, 52, 56, 58, 59, 66, 68, and 82 or low risk HPV types 6, 11, 40, 43, 53, 61, 67, 69, 70, 71, 72, 81, and 83. Using the present assay with these HR HPV probes, cross-reactivity between low risk HPV types and high risk HPV probes is reduced. See, for example, U.S. patent application Ser. No. 12/426,076.

The present invention also provides a method for determining the presence of a target nucleic acid molecule, such as HPV, in a sample in about 2 hours or less, about 2.5 hours or less, about 3 hours or less, about 3.5 hours or less, about 4 hours or less, about 5 hours or less, about 6 hours or less, about 7 hours or less, about 8 hours or less, about 12 hours or less, about 24 hours or less, in other aspects, less than about 3.5 hours for at least 10 samples using the methods discussed above. One reason why the presence of HPV or other target nucleic acid molecules can be determined in short periods of time is because the method does not amplify the target nucleic acid molecule prior to detection. Instead of target amplification, signal amplification may be used to accurately detect the presence of HPV or other target nucleic acid molecules. In an aspect, the methods of the disclosure may include a signal amplification step. In an aspect, the methods of the disclosure do not include a target amplification step. In another aspect, the methods of the disclosure may include a signal amplification step and no target amplification step.

The present disclosure also provides methods and assays for detecting cancer, for example cervical cancer, by detecting the presence of a target nucleic acid molecule, such as HPV, in a sample in about 2 hours or less, about 2.5 hours or less, about 3 hours or less, about 3.5 hours or less, about 4 hours or less, about 5 hours or less, about 6 hours or less, about 7 hours or less, about 8 hours or less, about 12 hours or less, about 24 hours or less, in other aspects, less than about 3.5 hours for at least 10 samples using the methods and assays discussed above.

It will be understood to those skilled in the art that the present invention can be carried out on a number of platforms including, but not limited to, tubes, dipsticks, microarrays, microplates, 384 well plates, other microtiter plates and microfluidic systems. It will be understood to those skilled in the art that the present, as relevant to developing countries, can utilize low technology methods such as dropper bottles, rubber bulbs, Pasteur pipettes, or squirt bottles for steps involving movement of liquid. These devices deliver relatively precise volumes within the approximate ranges that are needed for the assay. In an aspect, the methods of the disclosure do not include automatic pipettors or other battery powered or energy powered pipetting devices.

Another aspect of the present invention provides a collection medium into which samples containing the target nucleic acid are collected. The collection medium provides sample stability for several days, several weeks, or several months. For example, the collection medium may provide sample stability for at least 1 week, at least 2 weeks, at least 3 weeks, at least 4 weeks, at least 1 month, at least 2 months, at least 3 months, at least 4 months, at least 5 months, at least 6 months, from about 1 week to about 4 weeks, from about 1 month to about 3 months, from about 3 to about 4 months, or from about 3 month to 6 months. In another aspect, the collection medium provides sample stability for at least 21 days at 33° C. or at least 6 months at 20° C. In an aspect the above sample is a cervical cell sample or a human cervical cell sample. Suitable collection media are described herein. In one aspect, the collection medium comprises, consists of, or consists essentially of NP-40, deoxycholate, Tris-HCl, EDTA, NaCl, and sodium azide. In other aspects, the collection medium comprises, consists of, or consists essentially of 1.0% NP-40, 0.25% sodium deoxycholate, 50 mM Tris-HCl, 25 mM EDTA, 150 mM NaCl, and 0.05% sodium azide.

Another aspect is a detergent-containing wash buffer comprising, consisting of, or consisting essentially of 40 mM Tris pH 8.2, 100 mM NaCl, 0.1% to 0.5% Triton X-100, and 0.05% sodium azide. Yet another aspect is a detergent-free wash buffer comprising, consisting of, or consisting essentially of 40 mM Tris pH 8.2, 100 mM NaCl, and 0.05% sodium azide.

Sample Conversion for Recovery, Detection, and Analysis of Nucleic Acid Molecules An aspect relates to adding a collection medium to a sample which has been previously prepared for diagnostic analysis. In one aspect, the sample to which the collection medium is added has been previously prepared using a liquid based cytology (LBC) assay. LBC media can contain tissue fixatives such as alcohol and formalin which serve to stabilize the sample, inhibit bacterial growth, preserve cell morphology and diagnostic clusters, and assure the preparation of a tissue monolayer cytology slides. However, many compositions used to preserve biological samples, such as SUREPATH, contain alcohol or formalin which can be detrimental to analyzing nucleic acid molecules. In an aspect, the cytology slides contain cervical cell samples or any other biological sample capable of being evaluated. In an aspect, the SUREPATH media is used to prepare LBC sample.

In addition to cytology preparation, LBC samples can be used for detection of disorders, such as common sexually transmitted pathogens, including Human Papillomavirus (HPV), *Neisseria gonorrhoeae* (GC), and *Chlamydia trachomatis* (CT), among others. As a supplement to its application as a screening tool, LBC samples can be used to monitor patients' viral clearance after treatment for a particular disease, informing further follow-up and treatment regimens. In an aspect, HPV testing of LBC samples can be used to monitor patients' viral clearance after treatment for a cervical-based disease.

Figure 6:
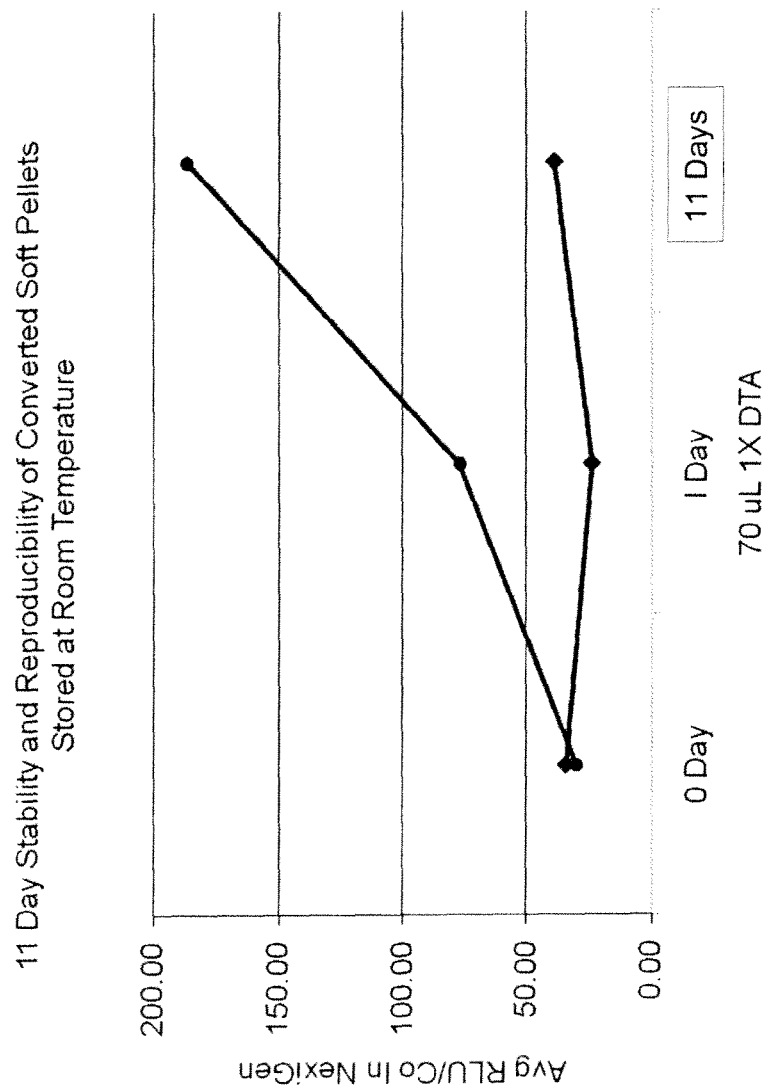
FIG. 6 shows a system for detecting the presence of a target nucleic molecule acid in a sample including a heater configured for heating multiple samples; a luminometer; and a monitor.

In an aspect, a biological sample is collected and preserved in a media, such as the SUREPATH media. The preserved media containing the biological sample is stored until further processing is required. The preserved media containing the biological sample can be removed and suspended in water thereby forming a "soft pellet." A portion of the soft pellet may be removed and analyzed on a slide. In an aspect, the sample is prepared using a LCB assay. Instead of adding more preservation media, such as SUREPATH, to the remaining soft pellet suspension, the detergent-based collection media described herein may be added to the remaining biological sample. This is advantageous in that a sample dispersed in the detergent-based collection media described herein can be directly analyzed in a nucleic acid molecule detection assay. Additionally, the biological sample suspended in the detergent-based collection medium is stable for at least 11 days at room temperature (FIG. 6).

Any of the disclosed detergent-based collection media are capable of being added to the soft pellet. In another aspect, a detergent and chelator media may be used to resolubilize the pellet. In a non-limiting aspect, a collection media including about 0.5% to about 2.0% NP-40, about 0.10% to about 0.40% sodium deoxycholate, about 25 mM to about 75 mM Tris-HC1, about 10 mM to about 50 mM EDTA, about 50 mM to about 200 mM NaCl, and about 0.01% to about 0.10% sodium azide can be used to solubilize the soft pellet. After the addition of the detergent-based collection media, the soft pellet sample may be analyzed in conjunction with any of the methods or assays described herein.

Kit

Also provided is a kit for the detection of a target nucleic acid molecule in a sample, the kit comprising, consisting of or, or consisting essentially of:
- a) a collection medium;
- b) a denaturation reagent;
- c) at least one polynucleotide probe;
- d) a bead coated with a first anti-hybrid antibody;
- e) a detection reagent comprising a second anti-poly hybrid antibody, wherein the second antibody is detectably labeled;
- f) a wash buffer; and
- g) a second detection reagent comprising a substrate for the label on the second antibody.

The collection medium, denaturation reagent, bead, first and second antibodies, polynucleotide probes, detection reagents, and wash buffers have been previously described.

The kit may also include instructions for describing procedures associated with the disclosed methods and assays. The kit may also include a means for transcribing patient information. In an aspect, the means includes paper, a computer, or a device capable of transmitting patient information. The kit can include all the necessary components to complete the methods at the same location where the patient sample is taken.

In an aspect, the kit may include color coded reagents associated with the detection assay. The reagent vials are color coded for ease of use and can be included in a kit. The reagent bottles may also be identified by symbols, letters, or other known identifiers.

As the individual components of the kit come together in an easy to use platform, one advantage of the kit described herein is that it provides for immediate testing o samples. This allows for rapid determination of patient results.

In an aspect, methods of the disclosure can include the collection and processing of patient samples in the field. In one aspect, after the samples are collected, some of the method steps are conducted at the same location where the patient samples are collected. In another aspect, all of the method steps can be conducted at the same location where the samples are collected. The location may be a village, clinic, laboratory, or communal area where individuals receive medical checkups and evaluations. The location may be permanent or temporary. In an aspect, the nucleic acid molecule is detected at a location, such as a laboratory or clinic, which is different from where the samples are taken. In an aspect, the kit is designed for use in a developing country or geographical areas where access to medical care is not readily available.

System

Figure 7:
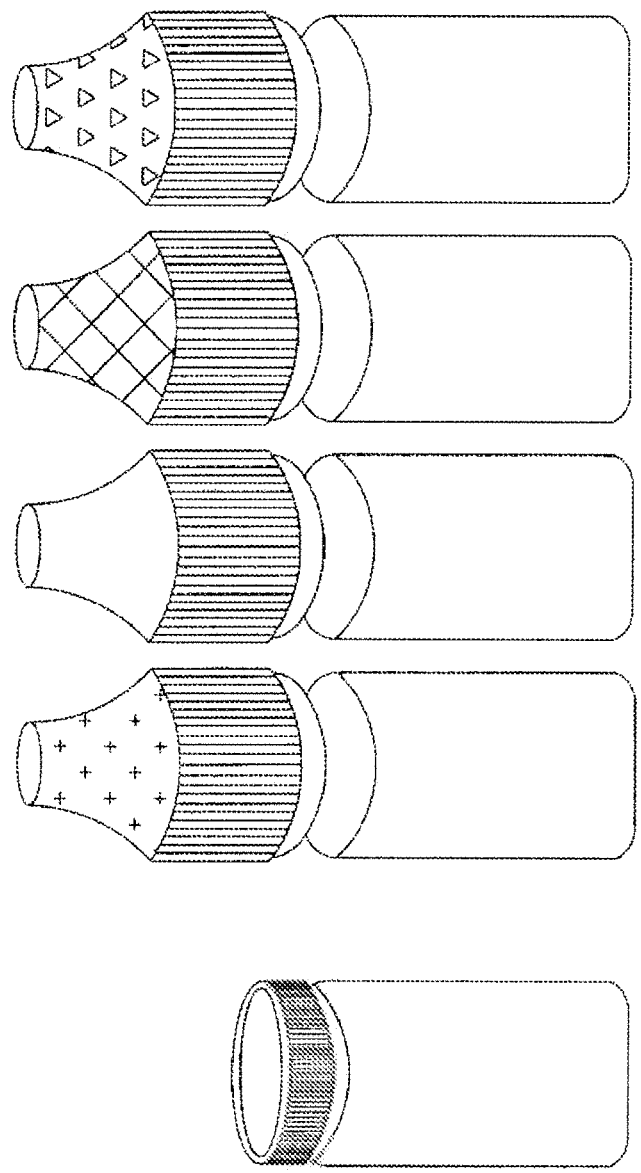
FIG. 7 shows different reagents associated with the detection assay. The reagent vials are color coded for ease of use and can be included in a kit.
Figure 8:
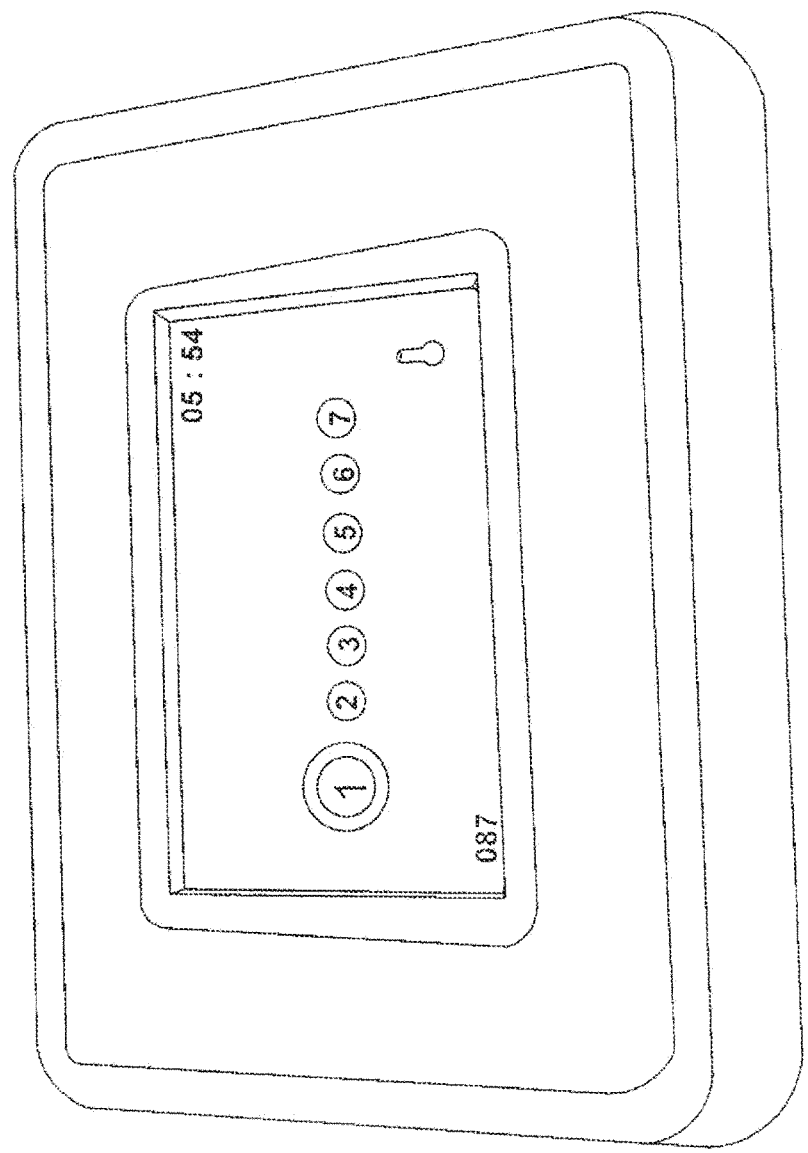
FIG. 8 shows a monitor used in conjunction with the system for detecting the presence of nucleic acid molecules.
Figure 9:
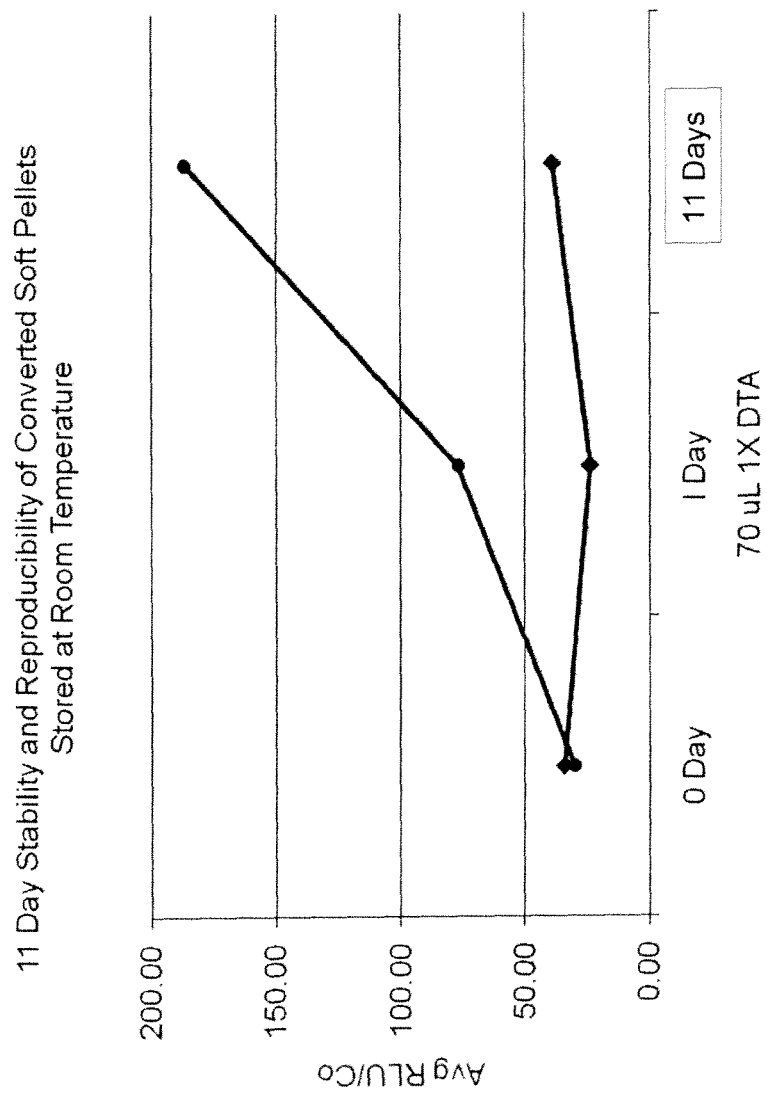
FIG. 9 shows 11 day stability data for soft pellets suspended in a detergent-based collection medium and stored at room temperature.

In an aspect, the sample may be analyzed using a portable system for detecting the presence of a target nucleic molecule acid in a sample. The portable system may include a heater configured for heating multiple samples; a luminometer configured to detect the chemiluminescence of a target nucleic acid molecule on a support coated with a first antibody and conjugated to a second antibody labeled with a detectable marker; and a monitor configured to report chemiluminescence data (FIG. 7). In an aspect, the heater is a combination heater/shaker. In an aspect, the system is configured to simultaneously analyze 90 samples at a time together with 6 controls (96 samples altogether). In an aspect, both the luminometer and the heater are configured to simultaneously analyze 90 samples at a time together with 6 controls (96 samples altogether). The system is also capable of reporting the results of at least 500 samples at a time. The portable system and associated reagents are set forth in FIGS. 6, 7, and 8.

Without being limited, the individual components of the portable system can be easily transported by an individual, such as a doctor or laboratory technician, and weighs less than 10 pounds, less than 20 pounds, less than 30 pounds, or less than 40 pounds. In another aspect, the entire portable system for detecting target nucleic acid molecules weighs less than 20 pounds, less than 30 pounds, less than 40 pounds, or less than 50 pounds, or less than 100 pounds and is designed for easy transportation.

The portable system and assay can be designed for use in the field or location where samples are collected and require a small footprint of bench-top work space (for example, about 25×50 cm or less). In an aspect, the portable system is configured to work without electricity, mains, or running water. The portable system may also run entirely on batteries. The portable system can be designed for use with the described kit, assays, with the methods described herein. Together, the kit and portable system provide an efficient and rapid way to analyze samples and detect nucleic acid samples in developing countries or other areas which may lack sophisticated laboratory equipment or facilities for analyzing laboratory samples.

It is noted that when ranges are described herein, any number within that range is contemplated in the inventions described herein. The entire contents of all patents, patent applications, scientific publications, etc. listed are incorporated in their entirety by reference. The examples below are not meant to limit the scope of the invention.

EXAMPLES

Example 1

Assay Using Cervical Samples and HPV probes

A total of 324 physician collected cervical samples were collected in a detergent based collection medium and tested for the presence of high-risk HPV.

A 1 ml sample was vortexed to homogenize the sample and a 50 μl aliquot was removed and combined with 25 μl of denaturation reagent (1.75 N NaOH) in the assay microplate. This was shaken to mix and incubated at 70° C. for 30 minutes to create single stranded DNA. To this, 40 μl of a neutralization buffer (probe diluent −2.2M BES, 2.6% PAA, 0.7 N NaOH and 0.05% sodium azide) containing RNA probes for 16 HPV types was added to create a neutral pH and incubated at 68.5° C. for 10 minutes.

Following this, 10 μl of antibody conjugated paramagnetic beads (approximately 1 μm carboxylated SERADYN beads from Thermo Fisher) were added to the reaction and incubated for an additional 30 minutes at 68.5° C. The RNA probes and DNA target molecules that were complementary to each other bind and create RNA-DNA hybrids. The hybrids then captured by a RNA-DNA hybrid specific antibody coated on the paramagnetic SERADYN beads.

Following incubation, the paramagnetic beads are separated from the liquid phase/supernatant by exposure to a magnetic field. The supernatant waste is removed by decanting and 35 μl of detection reagent 1 (secondary antibody conjugated enzyme comprising a monoclonal anti-RNA-DNA hybrid antibody conjugated to alkaline phosphatase) is added and incubated at 45° C. for 30 minutes. The secondary antibody binds the RNA-DNA hybrid-antibody-conjugated paramagnetic bead complex. Non-bound secondary antibody is washed away using a detergent based wash buffer (40 mM Tris, pH 8.2, 100 mM NaCl, 0.1% Triton-X 100 and 0.05% sodium azide).

A substrate (dioxetane-based substrate from ABI, called DCP Star, with Emerald II enhancer) is added to the washed beads and wells that contain high-risk HPV DNA create light that is detectable by a luminometer and measured in RLUs (relative light units). An assay positive standard containing 1 μg/ml of HPV DNA is used to establish the positive cutoff. All sample RLU values are divided by the RLU value for the positive standard creating a RLU/CO (RLU to cutoff value). Results are reported in RLU/CO and anything greater than or equal to 1.0 is considered positive.

Example 2

Stability Testing

Figure 3:
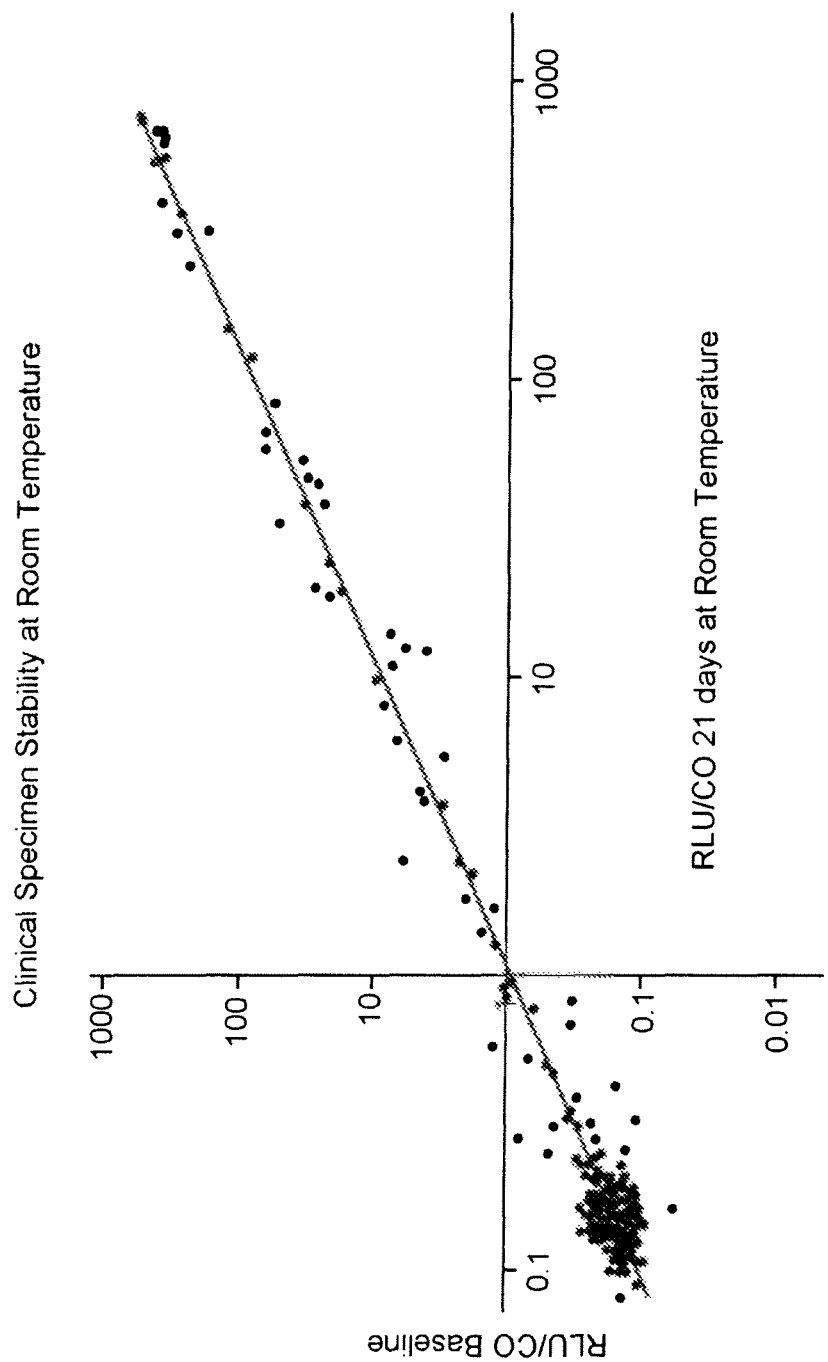
FIG. 3 shows clinical specimen stability at room temperature for 21 days.
Figure 4:
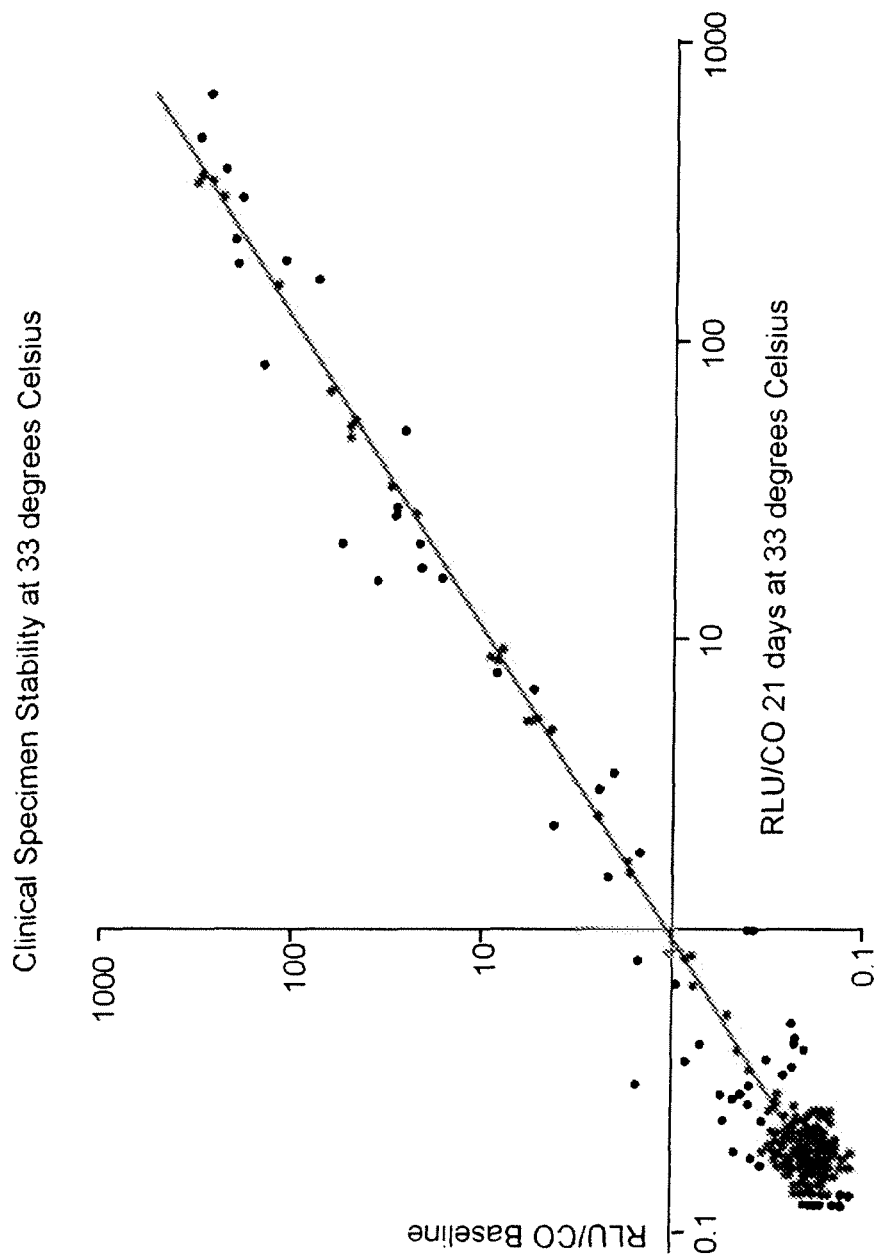
FIG. 4 shows clinical specimen stability at 33° C. for 21 days.

Following initial testing, samples were stored at room temperature and 33° C. to observe the stability of the samples. Testing was conducted as far as 21 days post collection. FIGS. 3 and 4 demonstrate that the RLU/CO value for each sample does not change with time up to 21 days. A 2×2 analysis comparing baseline results to the results after 21 days of storage and scatter plot analysis demonstrated the linearity of the RLU/CO values with time. Based on these data, it is possible to conclude that samples collected and stored at either room temperature or 33° C. for as long as 21 days provide comparable RLU/CO values as tested at baseline. Using linear mixed model comparison of RLU/CO values against the temperature of storage the P values are 0.8803 for room temperature and 0.9517 for samples stored at 33° C. indicating that values are equal.

Example 3

Limit of Detection Studies

Figure 5:
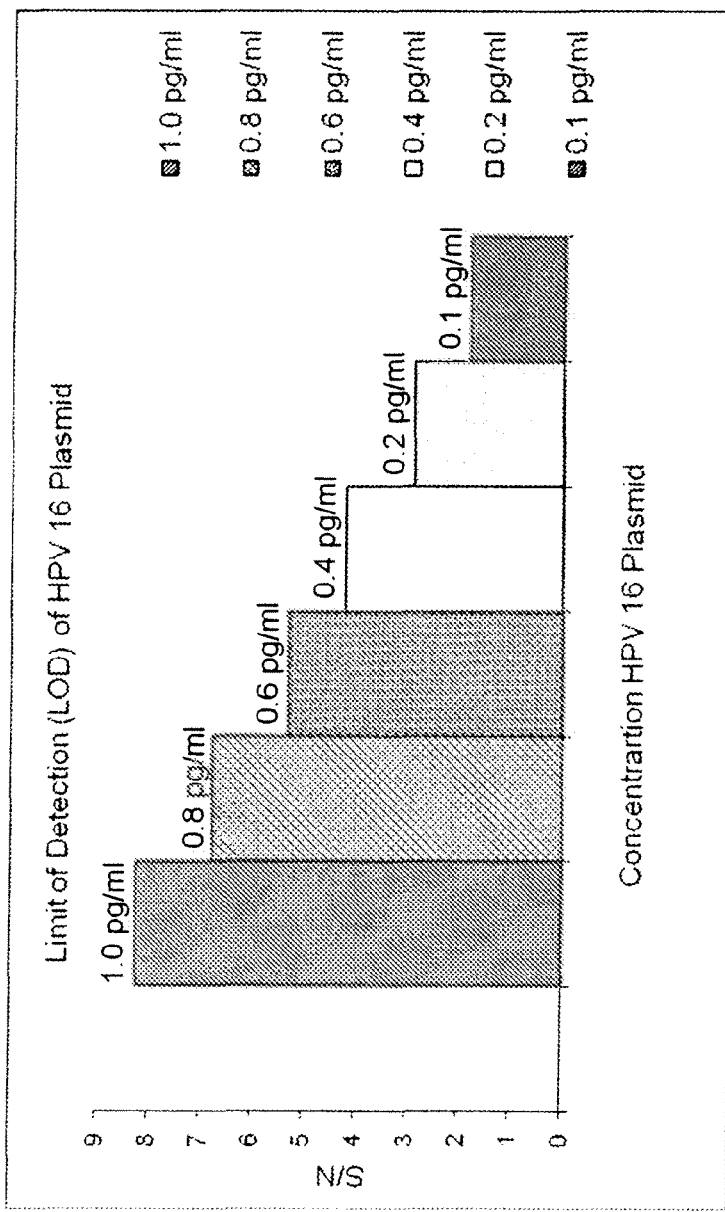
FIG. 5 shows test results demonstrate an S/N≥2.0 for a 0.2 pg/ml HPV 16 plasmid which is equivalent to 1000 copies of HPV 16 DNA.

The limit of detection (LOD) of HPV 16 was measured by serial dilution of HPV-16 plasmid target in the collection medium. The test results demonstrate a S/N≥2.0 for a 0.2 μg/ml HPV 16 plasmid which is equivalent to 1000 copies of HPV 16 DNA. See FIG. 5. In addition, three-week stability studies were performed on clinical specimens at elevated temperatures to mimic the conditions in an area subject to relatively elevated temperatures, such as Rwanda. All biologically labile kit components (RNA probe, capture antibody, detection antibody-enzyme conjugate, and substrate) were stabilized as part of the production process and monitored for stability over 18 months at 37° C.

Example 4

SUREPATH Pellet Conversion and Recovery of Nucleic Acids

In this example, the typical workflow for SUREPATH pellet conversion and nucleic acid recovery is described. Workflow for SUREPATH media includes initial collection of the primary sample, which can be cytobrush employed for collection of cervical epithelium cells at a transition zone or sample collection point. An average of $2 \times 10^{\wedge}8$ cervical cells are collected per brush, which can be preserved in 10 mL of SUREPATH media in a collection vial. The vial can be sealed and cells incubated in the fixative media at room temperature or 4° C. until further processing is performed. The cell suspension can then be subjected to an automated density gradient purification scheme, and the resulting cellular pellet, with an average total cell number of $1.6 \times 10^{1 \wedge}8$ cells, can be suspended in a final volume of 1 mL water. This water pellet can be referred to as a "soft pellet" or "undiluted soft pellet".

200 uL of the soft pellet can be used in an automated slide preparation protocol for cytology, leaving on average $1.3 \times 10^{\wedge}8$ total cells in an 800 μL volume. After removal of the 200 aliquot for slide preparation, 1-2 mL of fresh SUREPATH media can be added to the remaining 800 μL soft pellet to stabilize and preserve the soft pellet in case the slide must be remade. In most cases, this remaining 2-3 mL sample is destroyed after cytology results are reported.

The detergent-based medium described herein can be added to the remaining 800 μL soft pellet. Any of the detergent-based collection medium described herein can be added to the remaining 800 μL soft pellet. In an aspect, the media may contain 1.0% NP-40, 0.25% sodium deoxycholate, 50 mM Tris-HCl, 25 mM EDTA, 150 mM NaCl and 0.05% sodium azide. After the addition of the detergent-based collection media, the soft pellet sample can be analyzed in conjunction with any of the methods or assays described herein.

What is claimed is:

1. A composition comprising:
   (a) a biological sample suspended in a collection medium, wherein said collection medium comprises NP-40, sodium deoxycholate, and EDTA;
   (b) a denaturation reagent;
   (c) at least one polynucleotide probe capable of binding to a target nucleic acid molecule;
   (d) a support coated with a first antibody; and
   (e) a second antibody labeled with a detectable marker.

2. The composition of claim 1, wherein said biological sample is a cervical cell sample.

3. The composition of claim 1, wherein said collection medium comprises about 0.8% to about 1.5% NP-40, about 0.20% to about 0.40% sodium deoxycholate, and about 20 mM to about 40 mM EDTA.

4. The composition of claim 1, wherein a RLU/CO value for said biological sample does not change with time during at least a 21 day period when stored in said collection medium at 33° C.

5. The composition of claim 1, wherein said at least one polynucleotide probe is selected from the group consisting of probes for HPV high risk types 16, 18, 26, 31, 33, 35, 39, 45, 51, 52, 56, 58, 59, 66, 68, and 82.

6. The composition of claim 1, wherein said collection medium further comprises sodium azide.

7. A composition comprising:
   (a) a biological sample suspended in a collection medium comprising NP-40, sodium deoxycholate, and EDTA; and
   (b) a polynucleotide probe.

8. The composition of claim 7, wherein said collection medium further comprises sodium azide.

9. The composition of claim 7, wherein said biological sample is a cervical cell sample.

10. The composition of claim 7, wherein a RLU/CO value for said biological sample does not change with time during at least a 21 day period when stored in said collection medium at 33° C.

11. The composition of claim 7, wherein nucleic acid molecules in said biological sample are denatured.

12. The composition of claim 7, further comprising:
    (c) a support coated with a first antibody.

13. The composition of claim 12, further comprising:
    (d) a second antibody.

14. The composition of claim 13, wherein said second antibody is labeled with a detectable marker.

15. A kit for the detection of a target nucleic acid molecule in a sample, comprising,
    a) a collection medium comprising NP-40, sodium deoxycholate, and EDTA;
    b) a denaturation reagent;
    c) a support coated with a first anti-hybrid antibody;
    d) a detection reagent comprising a second anti-poly hybrid antibody, wherein the second antibody is detectably labeled;
    e) a detergent-based wash buffer; and
    f) a second detection reagent comprising a substrate for the label on the second antibody.

16. The kit of claim 15, wherein said collection medium further comprises sodium azide.

17. The kit of claim 15, wherein said detergent-based wash buffer comprises about 0.8% to about 1.5% NP-40, about 0.20% to about 0.40% sodium deoxycholate, about 30 mM to about 60 mM Tris-HCl, about 20 mM to about 40 mM EDTA, about 100 mM to about 200 mM NaCl, and sodium azide.

18. The kit of claim 15, wherein said detergent-based wash buffer comprises about 40 mM Tris pH 8.2, 100 mM NaCl, 0.1% - 0.5% Triton x-100, and 0.05% sodium azide.

19. The kit of claim 15, further comprising a probe diluent, wherein the diluent comprises BES, polyacrylic acid, NaOH and sodium azide.

20. The kit of claim 15, wherein the denaturation reagent is 1.75 N NaOH.

21. The kit of claim 15, further comprising at least one polynucleotide probe capable of binding to human papillomavirus (HPV) and genetic variants thereof.

22. The kit of claim 21, wherein said at least one polynucleotide probe is selected from the group consisting of probes for HPV high risk types 16, 18, 26, 31, 33, 35, 39, 45, 51, 52, 56, 58, 59, 66, 68,and 82.

23. The kit of claim 15, further comprising an apparatus configured to detect the presence of a target nucleic acid in a sample.

24. The kit of claim 23, wherein said system is a luminometer.

* * * * *